United States Patent
Kogawara

(10) Patent No.: US 10,395,360 B2
(45) Date of Patent: Aug. 27, 2019

(54) INSPECTION SYSTEM, CONTROLLER, INSPECTION METHOD, AND INSPECTION PROGRAM

(71) Applicant: OMRON Corporation, Kyoto-shi, Kyoto (JP)

(72) Inventor: Toru Kogawara, Kyoto (JP)

(73) Assignee: OMRON Corporation, Kyoto-shi (JP)

( * ) Notice: Subject to any disclaimer, the term of this patent is extended or adjusted under 35 U.S.C. 154(b) by 23 days.

(21) Appl. No.: 15/785,467

(22) Filed: Oct. 17, 2017

(65) Prior Publication Data

US 2018/0211372 A1 Jul. 26, 2018

(30) Foreign Application Priority Data

Jan. 20, 2017 (JP) .................................. 2017-008255

(51) Int. Cl.
| | | |
|---|---|---|
| G06T 7/00 | (2017.01) | |
| G01N 21/88 | (2006.01) | |
| G06T 7/73 | (2017.01) | |
| H04N 5/232 | (2006.01) | |
| H04N 5/225 | (2006.01) | |

(52) U.S. Cl.
CPC ......... *G06T 7/001* (2013.01); *G01N 21/8806* (2013.01); *G06T 7/74* (2017.01); *H04N 5/2259* (2013.01); *H04N 5/23238* (2013.01); *G06T 2207/10004* (2013.01); *G06T 2207/30164* (2013.01); *G06T 2207/30204* (2013.01)

(58) Field of Classification Search
None
See application file for complete search history.

(56) References Cited

U.S. PATENT DOCUMENTS

| | | | | |
|---|---|---|---|---|
| 6,493,079 | B1* | 12/2002 | Piacentini | G06K 9/209 356/240.1 |
| 2007/0217672 | A1* | 9/2007 | Shannon | G06T 7/0006 382/152 |
| 2013/0329954 | A1 | 12/2013 | Ikeda et al. | |
| 2016/0238373 | A1* | 8/2016 | Featherstone | G01B 21/047 |
| 2018/0047208 | A1* | 2/2018 | Marin | G06T 11/001 |

FOREIGN PATENT DOCUMENTS

| | | |
|---|---|---|
| CN | 206638598 U | 11/2017 |
| JP | 2000-180382 A | 6/2000 |

OTHER PUBLICATIONS

Extended European search report (EESR) dated Apr. 5, 2018 in a counterpart European Patent application.

* cited by examiner

*Primary Examiner* — Heather R Jones
(74) *Attorney, Agent, or Firm* — Metrolex IP Law Group, PLLC

(57) ABSTRACT

An inspection system for inspecting a workpiece includes: an omnidirectional camera; a movement device for causing the workpiece to circle around the omnidirectional camera in a state where a posture of the workpiece is maintained; an acquisition unit for outputting a capturing instruction to the omnidirectional camera at a plurality of timings while the movement device causes the workpiece to circle around the omnidirectional camera, and for acquiring, from the omnidirectional camera, a plurality of input images indicating the workpiece from different directions; and an inspector for inspecting the workpiece by using the plurality of input images.

18 Claims, 18 Drawing Sheets

US 10,395,360 B2

INSPECTION SYSTEM, CONTROLLER, INSPECTION METHOD, AND INSPECTION PROGRAM

CROSS-REFERENCE TO RELATED APPLICATION

This application is based on Japanese Patent Application No. 2017-008255 filed with the Japan Patent Office on Jan. 20, 2017, the entire contents of which are incorporated herein by reference.

FIELD

The present disclosure relates to a technology for inspecting an object to be inspected by using an omnidirectional camera.

BACKGROUND

In a factory automation (FA) field, a technology for inspecting an external appearance of an object to be inspected by using a camera has been developed. Regarding this technology, JP 2000-180382 A (Patent Document 1) discloses a visual inspection device that can inspect, at a high speed, a surface of an object to be inspected randomly placed on a conveyor. More specifically, the visual inspection device captures an object to be inspected conveyed on a conveyor from different directions with a plurality of cameras. The visual inspection device then inspects the object to be inspected by using input images obtained by capturing the object to be inspected from different directions.

Patent Document 1: JP 2000-180382 A

SUMMARY

The visual inspection device disclosed in Patent Document 1 needs to include a plurality of cameras in order to capture an object to be inspected from various directions. This leads to high costs of the visual inspection device and a complicated configuration of the visual inspection device. Therefore, a technology for inspecting an external appearance of an object to be inspected from various directions with one camera is desired.

According to an aspect, an inspection system for inspecting an object to be inspected includes: an omnidirectional camera; a movement device configured to cause the object to be inspected to circle around the omnidirectional camera in a state where a posture of the object to be inspected is maintained; an acquisition unit configured to output a capturing instruction to the omnidirectional camera at a plurality of timings while the movement device causes the object to be inspected to circle around the omnidirectional camera, the acquisition unit being configured to acquire, from the omnidirectional camera, a plurality of input images indicating the object to be inspected from different directions; and an inspector configured to inspect the object to be inspected by using the plurality of input images.

It may be preferable that the movement device causes the object to be inspected to circle around the omnidirectional camera in a state where a constant distance is maintained from the omnidirectional camera to the object to be inspected.

It may be preferable that the movement device does not stop the object to be inspected while the object to be inspected is circling around the omnidirectional camera.

It may be preferable that the inspection system further includes: a storage configured to associate and store a reference image obtained by capturing in advance an object of a type identical to the object to be inspected from a different direction with a direction of the object shown in the reference image; and an identification unit configured to identify a first direction of the object to be inspected shown in a first input image of the plurality of input images and a second direction of the object to be inspected shown in a second input image of the plurality of input images. The inspector compares the reference image associated with the first direction with the first input image, compares the reference image associated with the second direction with the second input image, and inspects the object to be inspected based on a result of the comparison.

It may be preferable that the identification unit identifies the first direction based on a position of the object to be inspected at a capturing timing of the first input image, and a position of the omnidirectional camera, and identifies the second direction based on a position of the object to be inspected at a capturing timing of the second input image, and the position of the omnidirectional camera.

It may be preferable that different marks are put at different positions on a surface of the movement device. The plurality of marks are associated in advance with directions of the object to be inspected. The identification unit identifies each of the directions associated with each of the marks shown in the first input image as the first direction, and identifies each of the directions associated with each of the marks shown in the second input image as the second direction.

It may be preferable that the inspector: identifies the position of the object to be inspected shown in the first input image based on a positional relationship between the position of the object to be inspected at the capturing timing of the first input image and the omnidirectional camera, the inspector comparing the object to be inspected shown at the position with the reference image associated with the first direction; identifies the position of the object to be inspected shown in the second input image based on a positional relationship between the position of the object to be inspected at the capturing timing of the second input image and the omnidirectional camera, the inspector comparing the object to be inspected shown at the position with the reference image associated with the second direction; and inspects the object to be inspected based on a result of the comparison.

According to another aspect, a controller for controlling a movement device for moving an object to be inspected and an omnidirectional camera for capturing the object to be inspected includes: an acquisition unit configured to output, to the movement device, an instruction for causing the object to be inspected to circle around the omnidirectional camera in a state where a posture of the object to be inspected is maintained, to output a capturing instruction to the omnidirectional camera at a plurality of timings while the movement device causes the object to be inspected to circle around the omnidirectional camera, and to acquire, from the omnidirectional camera, a plurality of input images indicating the object to be inspected from different directions; and an inspector configured to inspect the object to be inspected by using the plurality of input images.

According to another aspect, an inspection method for inspecting an object to be inspected includes: causing the object to be inspected to circle around an omnidirectional camera in a state where a posture of the object to be inspected is maintained; outputting a capturing instruction to the omnidirectional camera at a plurality of timings while the object to be inspected is circling around the omnidirectional camera, and acquiring, from the omnidirectional camera, a plurality of input images indicating the object to be inspected from different directions; and inspecting the object to be inspected by using the plurality of input images.

According to another aspect, a non-transitory computer-readable storage medium storing an inspection program for inspecting an object to be inspected, the inspection program causing a computer to execute: causing the object to be inspected to circle around an omnidirectional camera in a state where a posture of the object to be inspected is maintained; outputting a capturing instruction to the omnidirectional camera at a plurality of timings while the object to be inspected is circling around the omnidirectional camera, and acquiring, from the omnidirectional camera, a plurality of input images indicating the object to be inspected from different directions; and inspecting the object to be inspected by using the plurality of input images.

In one aspect, an external appearance of an object to be inspected can be inspected from various directions with one camera.

The above and additional objects, features, aspects, and advantages of the present disclosure will become apparent in the following detailed description regarding one or more embodiments that will be understood in relation to accompanying drawings.

DETAILED DESCRIPTION

Embodiments will be described below with reference to the drawings. In the following description, the same component and constituent element are denoted with the same reference symbol. A name and function thereof are the same. Therefore, detailed descriptions thereof will not be repeated.

<First Embodiment>

[A. Inspection System 1]

Figure 1:
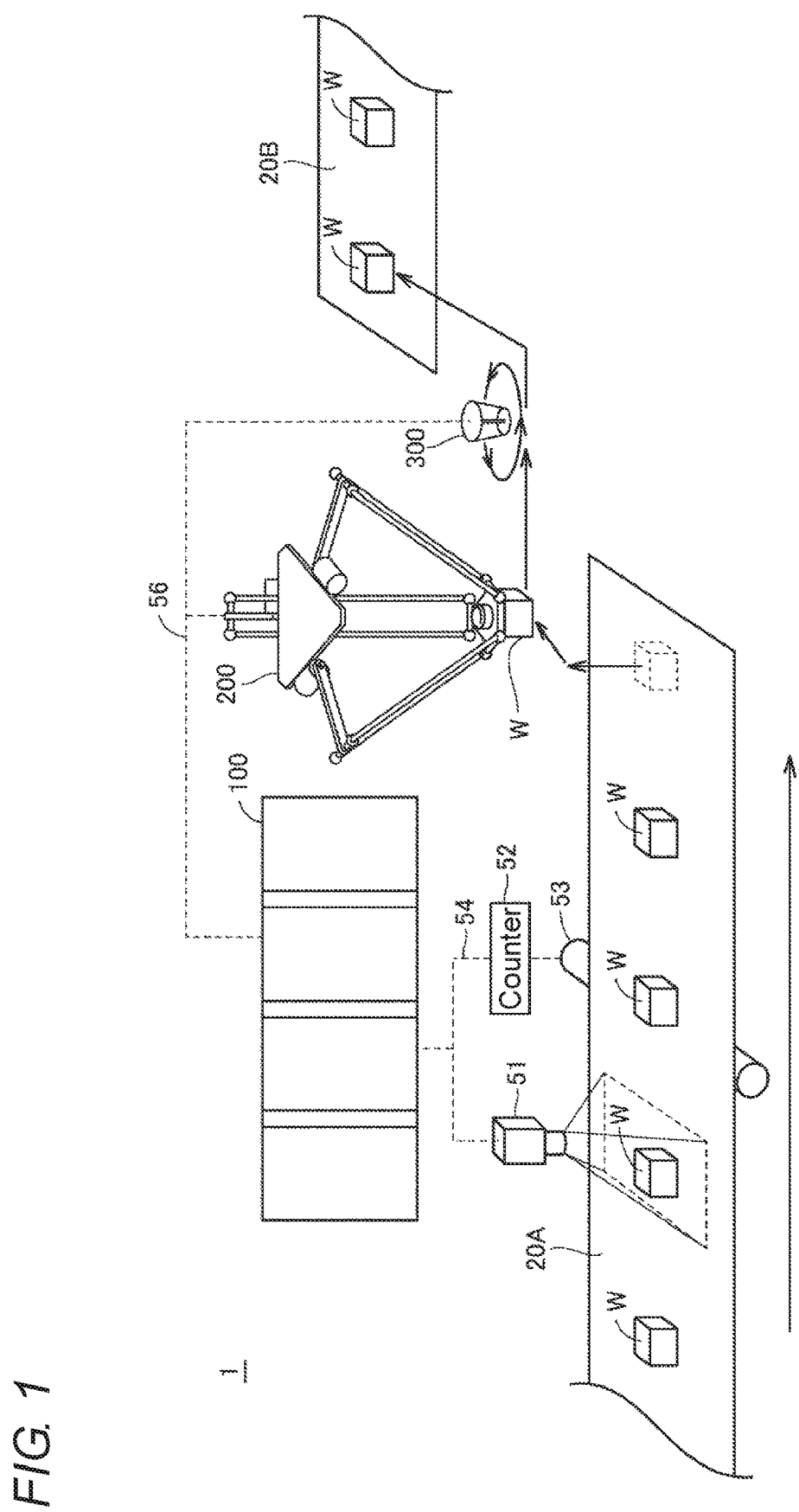
FIG. 1 is a schematic view illustrating a basic configuration of an inspection system according to a first embodiment.

With reference to FIG. 1, a basic configuration of an inspection system 1 according to an embodiment will be described. FIG. 1 is a schematic view illustrating a basic configuration of an inspection system 1 according to an embodiment.

As illustrated in FIG. 1, the inspection system 1 includes, for example, a controller 100, a robot 200 that serves as a movement device, and an omnidirectional camera 300.

The controller 100 is, for example, a programmable logic controller (PLC), and controls the entire inspection system 1. As one example, the controller 100 controls devices such as an image sensor 51, the robot 200, and the omnidirectional camera 300.

The controller 100 is connected, for example, to a field network 54 in a daisy chain with the image sensor 51 and a counter 52. As the field network 54, for example, EtherCAT (registered trademark) is employed. The controller 100 has a communication linkage with the robot 200 via a field network 56. As the field network 56, for example, EtherNET (registered trademark) is employed.

The inspection system 1 performs predetermined work on a workpiece W (object to be inspected) conveyed on a conveyor 20A. The workpiece W is a product or semi-finished product, and for example, may be an electronic component or a food.

The image sensor 51 regularly captures the conveyor 20A and detects the workpiece W from an obtained input image. As one example, the image sensor 51 detects the workpiece W by image processing such as template matching. A coordinate value of the workpiece W in the input image is output to the controller 100.

The counter 52 measures a movement amount of the conveyor 20A based on a pulse wave generated from an encoder 53. More specifically, the encoder 53 generates a pulse signal according to the movement amount of the conveyor 20A. The counter 52 receives the pulse signal from the encoder 53 and counts the number of pulses included in the pulse signal to measure the movement amount of the conveyor 20A. The counter 52 then transmits a counted value of the pulse wave to the controller 100 at constant communication intervals.

The controller 100 substitutes the coordinate value (camera coordinate system) of the workpiece W in the input image received from the image sensor 51 into a coordinate transformation equation determined in advance. The controller 100 then transforms the coordinate value of the camera coordinate system into a coordinate value of a world coordinate system. The world coordinate system is a coordinate system for controlling the robot 200. Every time the controller 100 receives the counted value from the counter 52, the controller 100 calculates the movement amount from last time on the conveyor 20A. The controller 100 then adds the movement amount to the coordinate value of the workpiece W indicated in the world coordinate system. The movement amount of the conveyor 20A corresponding to one count is set in advance. The controller 100 can track the workpiece W conveyed on the conveyor 20A by sequentially updating the coordinate value of the workpiece W indicated in the world coordinate system.

Based on the workpiece W having reached a range determined in advance on the conveyor 20A, the controller 100 sends a workpiece W pickup instruction to the robot 200. At this time, the controller 100 sequentially sends, to the robot 200, the coordinate value of the workpiece W on the conveyor 20A. This allows the robot 200 to grasp a current position of the workpiece W and to pick up the workpiece W on the conveyor 20A.

Subsequently, the robot 200 causes the workpiece W to circle around the omnidirectional camera 300 in a state where a posture of the workpiece W is maintained, and then the robot 200 moves the workpiece W to a conveyor 20B. "The state where the posture of the workpiece W is maintained" means a state where the workpiece W is fixed so as to prevent the workpiece W from rotating. This is a state where each surface of the workpiece W is always in the same direction during a circling process. The controller 100 captures the workpiece W while the workpiece W is circling around the omnidirectional camera 300. The controller 100 then inspects an external appearance of the workpiece W by using the input image obtained as a result of the capturing. Details of the inspection process will be described later.

Note that although FIG. 1 illustrates the example in which the inspection system 1 includes one controller 100, the inspection system 1 may include a plurality of controllers 100. Also, although FIG. 1 illustrates the example in which the inspection system 1 includes one robot 200, the inspection system 1 may include a plurality of robots 200. Also, although FIG. 1 illustrates the example in which the inspection system 1 includes one omnidirectional camera 300, the inspection system 1 may include a plurality of omnidirectional cameras 300.

[B. Workpiece W Capturing Process]

Figure 2A:
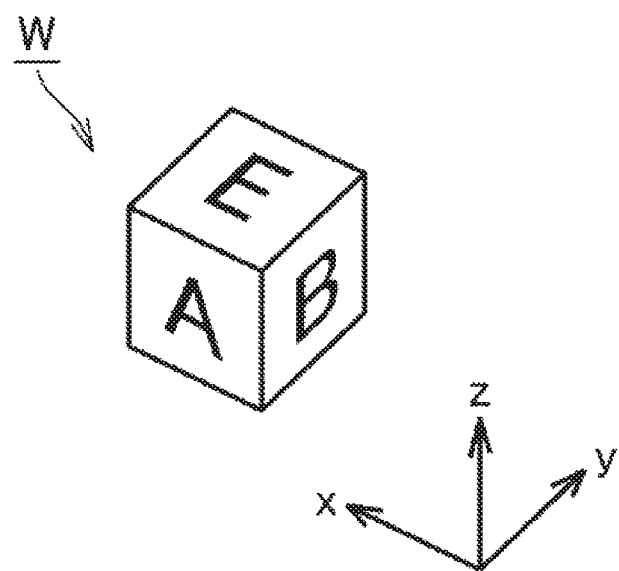
FIGS. 2A and 2B are views each illustrating one example of a workpiece, which is an object to be inspected.
Figure 2B:
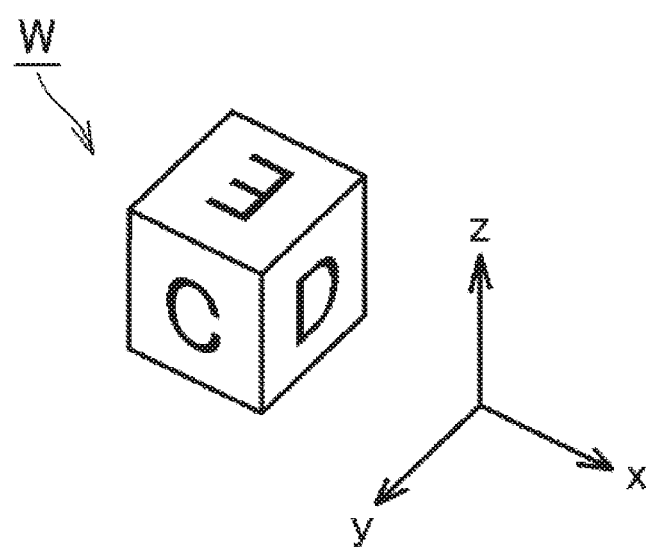
Figure 3:
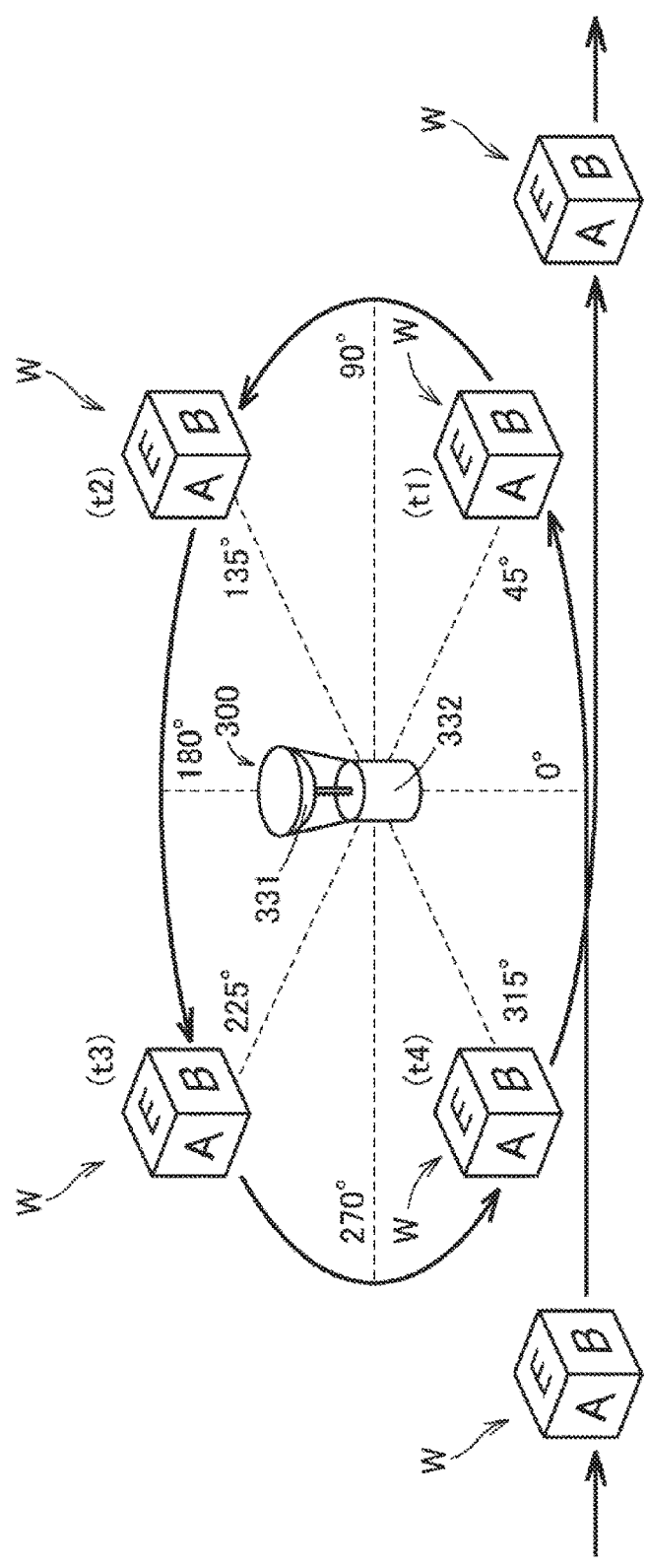
FIG. 3 is a view illustrating a process in which a robot according to a first embodiment is causing a workpiece to circle around an omnidirectional camera.
Figure 4:
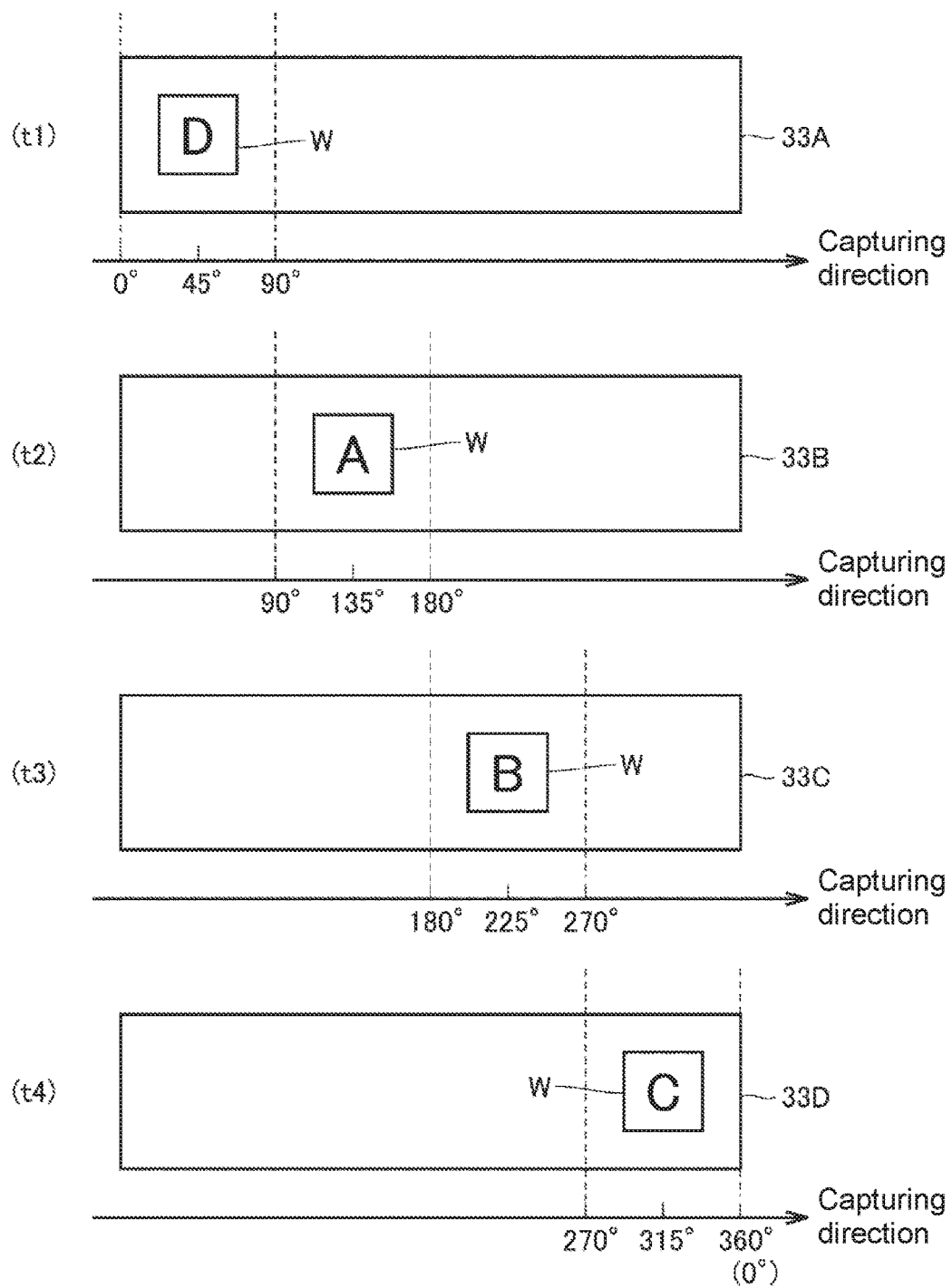
FIG. 4 is a diagram illustrating one example of input images obtained from an omnidirectional camera according to a first embodiment.

With reference to FIGS. 2 to 4, a workpiece W capturing process by the omnidirectional camera 300 will be described.

FIGS. 2A and 2B are views each illustrating one example of the workpiece W, which is an object to be inspected. For convenience of describing a direction of the workpiece W, the following description assumes that the workpiece W is a cube. As illustrated in FIG. 2, it is assumed that "an E surface" of the workpiece W is orthogonal to "an A surface" to "a D surface" of the workpiece W. It is assumed that "the A surface" of the workpiece W faces "the C surface" of the workpiece W. It is assumed that "the B surface" of the workpiece W faces "the D surface" of the workpiece W.

Note that a shape of the workpiece W, which is an object to be inspected, is not limited to a cube, but may be a polyhedron such as a rectangular parallelepiped, cylindrical, and another shape.

FIG. 3 is a view illustrating a process in which the robot 200 is causing the workpiece W to circle around the omnidirectional camera 300.

The omnidirectional camera 300 includes an omnidirectional mirror 331 and a capturing unit 332. The omnidirectional mirror 331 reflects light received from 360° around, and guides the reflected light to the capturing unit 332. This allows the omnidirectional camera 300 to capture an image 360° around.

As described above, the robot 200 causes the workpiece W to circle around the omnidirectional camera 300 in the state where the posture of the workpiece W is maintained. At this time, since the posture of the workpiece W is maintained, the external appearance of the workpiece W when viewed from the omnidirectional camera 300 changes at each position of the workpiece W.

Typically, a circling trajectory of the workpiece W is circular. That is, the robot 200 causes the workpiece W to circle around the omnidirectional camera 300 in a state where a constant distance is maintained from the omnidirectional camera 300 to the workpiece W. This allows, while the workpiece W is circling around the omnidirectional camera 300, the constant distance to be always maintained between the workpiece W and the omnidirectional camera 300. This results in a constant size of the workpiece W shown in an image obtained from the omnidirectional camera 300.

Typically, the robot 200 does not stop the workpiece W while the workpiece W is circling around the omnidirectional camera 300. This enables continuous inspection of the workpiece W that is sequentially conveyed, without stopping the workpiece W. Since a circling process of the workpiece W is performed during a pick and place operation of the workpiece W, even if the circling process of the workpiece W is added, a tact time does not increase.

While the robot 200 is causing the workpiece W to circle around, the robot 200 regularly transmits a position of the workpiece W (or a position of an arm) to the controller 100. When the received position of the workpiece W is on the circling trajectory determined in advance, the controller 100 determines that the robot 200 is causing the workpiece W to circle around the omnidirectional camera 300. The controller 100 outputs a capturing instruction to the omnidirectional camera 300 at a plurality of timings while the workpiece W is circling around the omnidirectional camera 300. This allows the omnidirectional camera 300 to capture the workpiece W from various directions. As a result, the controller 100 can acquire, from the omnidirectional camera 300, a plurality of input images indicating the workpiece W from different directions.

FIG. 4 is a diagram illustrating one example of the input images obtained from the omnidirectional camera 300. As one example, it is assumed that the controller 100 outputs the capturing instruction to the omnidirectional camera 300 at timing t1. As a result, an input image 33A indicating "the D surface" of the workpiece W is obtained. Similarly, it is assumed that the controller 100 outputs the capturing instruction to the omnidirectional camera 300 at timing t2. As a result, an input image 33B indicating "the A surface" of the workpiece W is obtained. Similarly, it is assumed that the controller 100 outputs the capturing instruction to the omnidirectional camera 300 at timing t3. As a result, an input image 33C indicating "the B surface" of the workpiece W is obtained. Similarly, it is assumed that the controller 100 outputs the capturing instruction to the omnidirectional camera 300 at timing t4. As a result, an input image 33D indicating "the C surface" of the workpiece W is obtained.

Intervals at which the capturing instruction is output are calculated by, for example, dividing, by a capturing count, a circling time needed for the workpiece W to circle around the omnidirectional camera 300 in a full circle. For example, when the circling time is one second and the capturing count is four times, the capturing interval will be 0.25 seconds (=¼). The circling time and the capturing count may be set in advance, and may be set arbitrarily.

Thus, by outputting the capturing instruction to the omnidirectional camera 300 at different timings while the workpiece W is circling around, the controller 100 can acquire, from one omnidirectional camera 300, the input images 30A to 30D indicating the workpiece W from different directions.

Note that FIG. 3 illustrates the example in which the workpiece W circles around the omnidirectional camera 300 in a full circle. However, the workpiece W does not necessarily have to circle around the omnidirectional camera 300 in a full circle. That is, the workpiece W is only required to circle around the omnidirectional camera 300 in at least part of a circle in the state where the posture is maintained. Also, the workpiece W does not need to circle around on a horizontal plane, and may circle around in any direction as long as the posture is maintained in part or all of a visual field of the omnidirectional camera 300.

[C. Functional Configuration of Controller 100]

Functions of the controller 100 will be described with reference to FIGS. 5 to 10.

Figure 5:
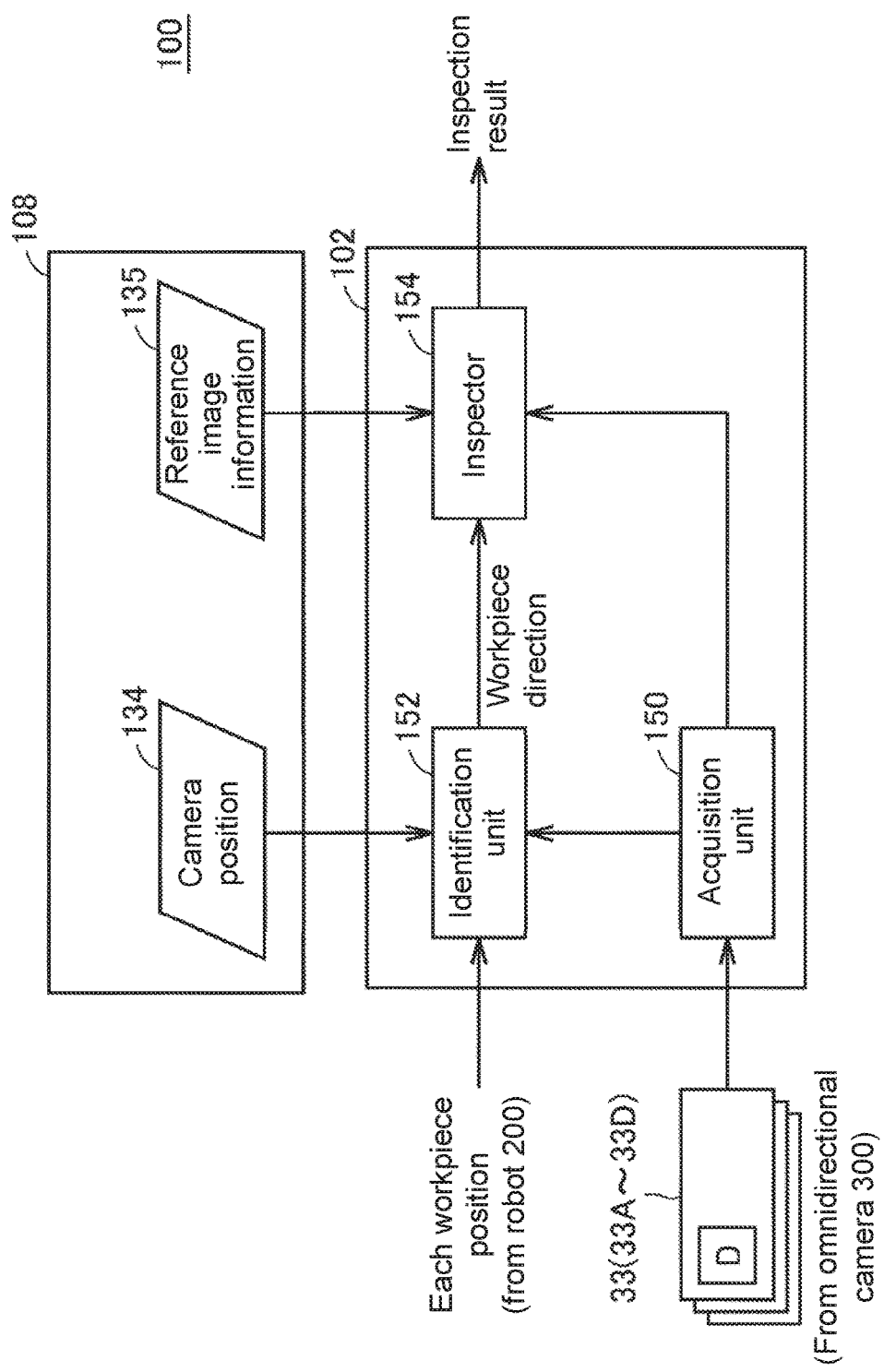
FIG. 5 is a diagram illustrating one example of a functional configuration of a controller according to a first embodiment.

FIG. 5 is a diagram illustrating one example of a functional configuration of the controller 100. As illustrated in FIG. 5, the controller 100 includes a processor 102 and a secondary storage device 108 as major hardware components. The processor 102 includes an acquisition unit 150, an identification unit 152, and an inspector 154 as functional components.

Note that although FIG. 5 illustrates the example in which the acquisition unit 150, the identification unit 152, and the inspector 154 are mounted on the controller 100, at least part of these functions may be mounted on another external device. For example, at least part of these functions may be mounted on an external device such as the image sensor 51 (refer to FIG. 1) or a server. In this case, the controller 100 and the external device cooperate to implement various processes according to an embodiment.

The following describes the acquisition unit 150, the identification unit 152, and the inspector 154 sequentially.

(C1. Acquisition Unit 150)

The acquisition unit 150 outputs the capturing instruction to the omnidirectional camera 300 at a plurality of timings while the workpiece W is circling around the omnidirectional camera 300. The acquisition unit 150 then acquires, from the omnidirectional camera 300, the plurality of input images indicating the workpiece W from different directions. Since a method for capturing the workpiece W has been described in FIG. 3, the method will not be described again.

(C2. Identification Unit 152)

As described above, the robot 200 causes the workpiece W to circle around the omnidirectional camera 300 in the state where the posture of the workpiece W is maintained. At this time, although the workpiece W itself does not rotate, a direction of the workpiece W changes when viewed from the omnidirectional camera 300. Hereinafter, the direction of the workpiece W with respect to the omnidirectional camera 300 is also referred to as "a workpiece direction." That is, the workpiece direction means an angle between a predetermined reference axis that passes on a circling plane and passes the center of the workpiece W, and a straight line connecting the workpiece W and the omnidirectional camera 300.

The identification unit 152 identifies the direction of the workpiece W at a capturing timing of the workpiece W. Various methods are employed as the method for identifying the direction of the workpiece W. The method for identifying the direction of the workpiece W will be described below with reference to FIGS. 6 to 9.

Figure 6:
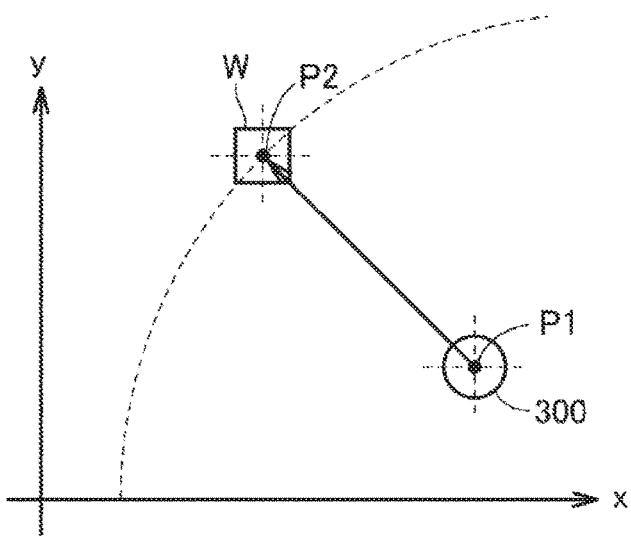
FIG. 6 is a diagram illustrating a first identification method for identifying a direction of a workpiece.

FIG. 6 is a diagram for describing a first identification method for identifying the direction of the workpiece W. FIG. 6 illustrates a position P1 of the omnidirectional camera 300, and a position P2 of the workpiece W at a predetermined timing at which the workpiece W is circling around the omnidirectional camera 300.

The position P1 of the omnidirectional camera 300 is prescribed, for example, as a camera position 134 (refer to FIG. 5). The camera position 134 may be set when the omnidirectional camera 300 is installed, and may be arbitrarily set by a user. The camera position 134 may be represented, for example, as a coordinate value on an xy plane, and may be represented as a coordinate value on an xyz plane. The coordinate value represents, for example, the center of the omnidirectional camera 300.

The position P2 of the workpiece W is acquired from the robot 200. More specifically, the controller 100 outputs, to the robot 200, a request for acquiring the position P2 of the workpiece W, simultaneously with outputting the capturing instruction of the workpiece W to the omnidirectional camera 300. This allows the controller 100 to acquire, from the robot 200, the position P2 of the workpiece W at the time of capturing the workpiece W. The position P2 of the workpiece W may be represented, for example, as a coordinate value on an xy plane, and may be represented as a coordinate value on an xyz plane. The coordinate value represents, for example, the center of the workpiece W.

The identification unit 152 identifies a direction from the position P1 of the omnidirectional camera 300 to the position P2 of the workpiece W as a capturing direction of the workpiece W. The capturing direction corresponds to the direction of the workpiece W when viewed from the omnidirectional camera 300. In a case where the direction of the workpiece W when the workpiece W reaches the circling trajectory is always identical, the capturing direction corresponds to the direction of the workpiece W one-to-one. That is, the direction of the workpiece W is always identical at an identical point on the circling trajectory. The identification unit 152 identifies the direction of the workpiece W from the capturing direction of the workpiece W based on correspondence between the capturing direction of the workpiece W and the direction of the workpiece W.

The identification unit 152 identifies the direction of the workpiece W for all the input images obtained from the omnidirectional camera 300 (for example, first and second input images). More specifically, the identification unit 152 identifies the direction of the workpiece W shown in the first input image based on the position of the workpiece W at the capturing timing of the first input image and the position of the omnidirectional camera 300. Similarly, the identification unit 152 identifies the direction of the workpiece W shown in the second input image based on the position of the workpiece W at the capturing timing of the second input image and the position of the omnidirectional camera 300.

Figure 7:
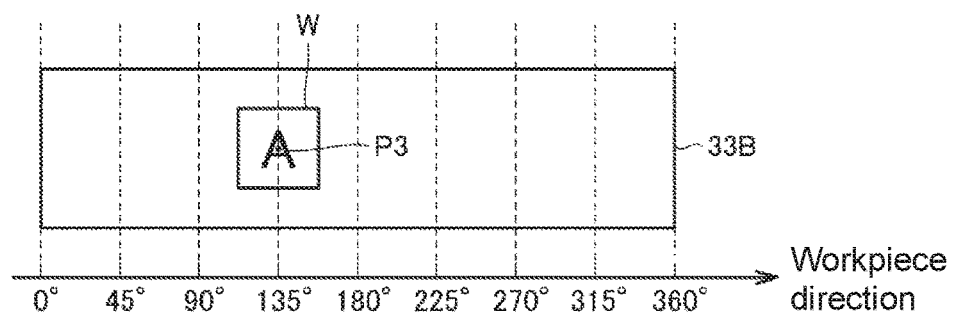
FIG. 7 is a diagram for describing a second identification method for identifying a direction of a workpiece.

Next, with reference to FIG. 7, another method for identifying the direction of the workpiece W will be described. FIG. 7 is a diagram for describing a second identification method for identifying the direction of the workpiece W.

FIG. 7 illustrates the input image 33B as one example of the input images obtained from the omnidirectional camera 300. When the omnidirectional camera 300 is used, a position in a long side direction of the input image 33B corresponds to a direction of a subject when viewed from the omnidirectional camera 300. That is, a coordinate value of the workpiece W in the input image 33B corresponds to the direction of the workpiece W one-to-one. Focusing on this point, based on correspondence between the coordinate value of the workpiece W in the input image and the direction of the workpiece W, the identification unit 152 identifies the direction of the workpiece W corresponding to the coordinate value of the workpiece W detected from the input image 33B. In the example of FIG. 7, the identification unit 152 identifies "135°" corresponding to a central position P3 of the workpiece W as the direction of the workpiece W at the capturing timing of the input image 33B.

Figure 8:
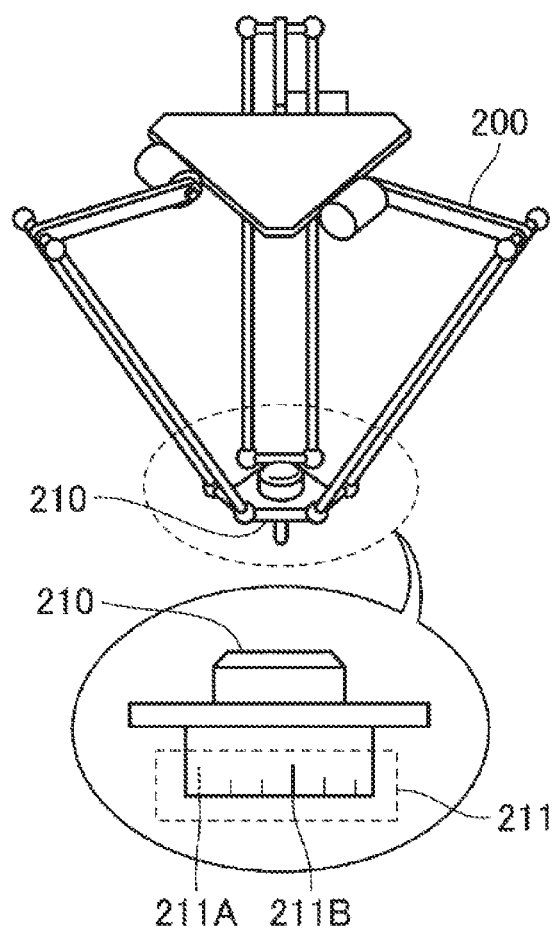
FIG. 8 is a view illustrating a grip portion 210, which is a portion with which a robot according to a first embodiment grips a workpiece.

Next, with reference to FIGS. 8 and 9, another method for identifying the direction of the workpiece W will be described. FIG. 8 is a view illustrating a grip portion 210, which is a portion with which the robot 200 grips the workpiece W.

FIG. 8 illustrates an enlarged view of the grip portion 210. Different marks are put at different positions on a surface of the grip portion 210. The marks serve as reference for identifying the direction of the workpiece W. Difference in the marks may be represented by difference in color, and may be represented by difference in shape. In the example of FIG. 8, a scale 211 is put on the grip portion 210, and the scale 211 is represented by marks 211A and 211B with different color.

Note that a position where the mark is put is not limited to the grip portion 210, but the mark is put at any position of the robot 200 if the position is included in a visual field of the omnidirectional camera 300.

Figure 9:
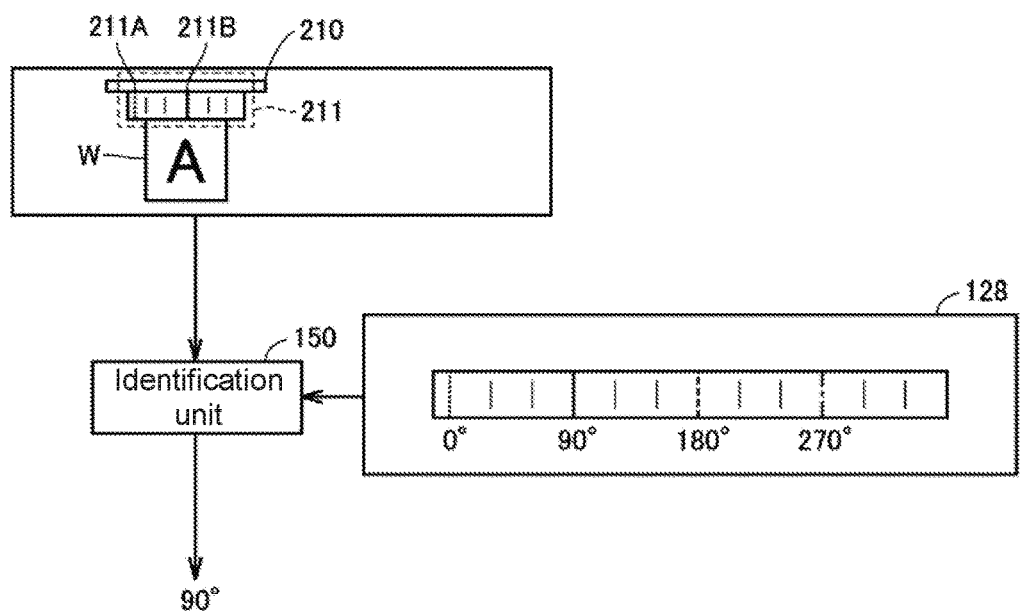
FIG. 9 is a diagram illustrating a third identification method for identifying a direction of a workpiece.

FIG. 9 is a diagram for describing a third identification method for identifying the direction of the workpiece W. The identification unit 152 detects the grip portion 210 from an input image 38 obtained by capturing the workpiece W. Next, the identification unit 152 identifies a type of mark shown at the center or substantial center of the detected grip portion 210. Subsequently, with reference to mark information 128 that prescribes the direction of the workpiece W for each type of mark, the identification unit 152 identifies a direction associated with the identified mark as the direction of the workpiece W. In the example of FIG. 9, "90°" associated with the mark 211B in the mark information 128 is identified as the direction of the workpiece W.

The identification unit 152 identifies the direction of the workpiece W for all the input images obtained from the omnidirectional camera 300 (for example, first and second input images). More specifically, the identification unit 152 detects the mark shown in the first input image and identifies the direction associated with the detected mark in the mark information 128. The identification unit 152 then identifies the identified direction as the direction of the workpiece W shown in the first input image. Similarly, the identification unit 152 detects the mark shown in the second input image and identifies the direction associated with the detected mark in the mark information 128. The identification unit 152 then identifies the identified direction as the direction of the workpiece W shown in the second input image.

Note that the above description assumes that the direction of the workpiece W when the workpiece W reaches the circling trajectory is always identical. However, the direction of the workpiece W when the workpiece W reaches the circling trajectory does not always need to be identical. Even if the direction of the workpiece W at the time is not always identical, if the direction of the workpiece W at one point on the circling trajectory is detected, the identification unit 152 can identify the direction of the workpiece W based on the direction of the workpiece W at the one point. Identifying the direction of the workpiece W at the one point is implemented, for example, by image processing such as template matching.

(C3. Inspector 154)

As described above, the acquisition unit 150 outputs the capturing instruction to the omnidirectional camera 300 at a plurality of timings while the workpiece W is circling around the omnidirectional camera 300. The acquisition unit 150 then acquires, from the omnidirectional camera 300, the plurality of input images indicating the workpiece W from different directions. The inspector 154 inspects the workpiece W, which is an object to be inspected, using the plurality of input images acquired by the acquisition unit 150.

Figure 10:
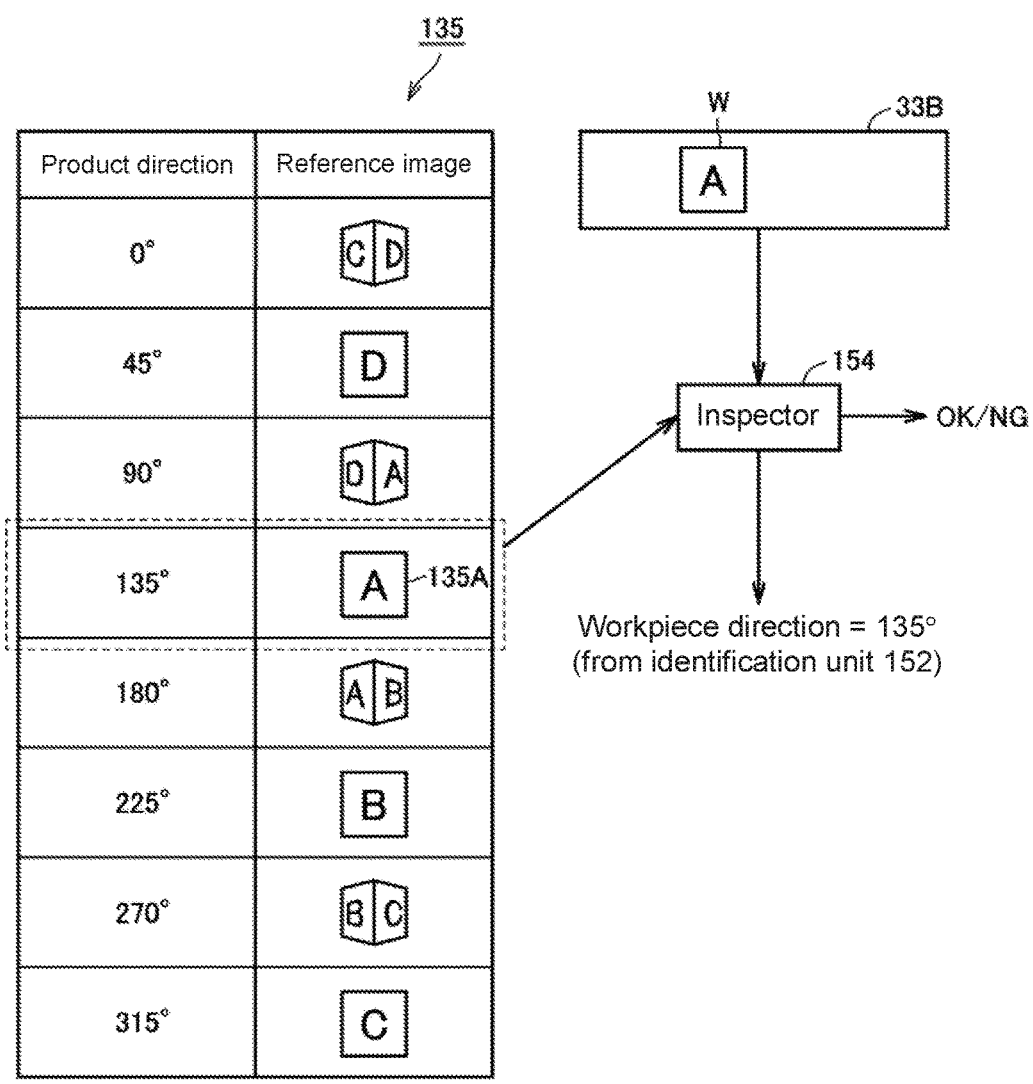
FIG. 10 is a conceptual diagram schematically illustrating an inspection process of a workpiece by an inspector.

With reference to FIG. 10, an inspection process of the workpiece W by the inspector 154 will be described. FIG. 10 is a conceptual diagram schematically illustrating the inspection process of the workpiece W by the inspector 154.

FIG. 10 illustrates the input image 33B acquired by capturing "the A surface" of the workpiece W as one example of the input image. The inspection process by the inspector 154 will be described below by citing, as an example, the input image 33B, which is one of the input images acquired from the acquisition unit 150.

The inspector 154 inspects the workpiece W shown in the input image 33B with reference to reference image information 135. The reference image information 135 includes a plurality of reference images obtained by capturing in advance an object of a type identical to the object to be inspected. Each reference image is associated with a direction of the object shown in the reference image. The reference image information 135 is prepared in advance before the inspection process is executed. For example, the reference image information 135 is stored in advance in the secondary storage device 108 of the controller 100 (refer to FIG. 12).

As described above, the identification unit 152 identifies the direction of the workpiece W shown in the input image 33B. The inspector 154 identifies the reference image associated with the direction of the workpiece W shown in the input image 33B with reference to the reference image information 135. In the example of FIG. 10, a reference image 135A associated with the direction of the workpiece W "135°" is identified. The inspector 154 compares the identified reference image 135A with the input image 33B, and then inspects the workpiece W shown in the input image 33B based on a result of the comparison.

Typically, the inspector 154 calculates a similarity group between each portion of the reference image 135A and the input image 33B while scanning the identified reference image 135A on the input image 33B. The inspector 154 then employs the maximum value of the similarity group as a similarity degree between the reference image 135A and the input image 33B. The similarity degree is represented, for example, by a correlated value between image information about the reference image 135A (for example, pixel value), and image information about the input image 33B (for example, pixel value). When the calculated similarity degree exceeds a value determined in advance, the inspector 154 determines that the external appearance of the workpiece W is normal. On the other hand, when the calculated similarity degree is equal to or less than the value determined in advance, the inspector 154 determines that the external appearance of the workpiece W is abnormal.

The inspector 154 performs such an inspection process on all the input images acquired from the acquisition unit 150 (for example, first and second input images). More specifically, the inspector 154 compares the reference image associated with the direction of the workpiece W shown in the first input image (first direction) with the first input image. Similarly, the inspector 154 compares the reference image associated with the direction of the workpiece W shown in the second input image (second direction) with the second input image. The inspector 154 inspects the workpiece W based on results of the comparison.

Typically, when all the calculated similarity degrees about the input images exceed the value determined in advance, the inspector 154 determines that the external appearance of the workpiece W is normal. On the other hand, when at least one of the calculated similarity degrees about the input images is equal to or less than the value determined in advance, the inspector 154 determines that the external appearance of the workpiece W is abnormal.

Typically, after cutting a portion in which the workpiece W is shown in the input image 33B, the inspector 154 compares the cut portion with the reference image 135A. More specifically, when the omnidirectional camera 300 is used, a position where the workpiece W is shown in the input image 33B depends on a positional relationship between the workpiece W and the omnidirectional camera 300. Focusing on this point, the inspector 154 identifies the position of the object to be inspected shown in the input image 33B based on the positional relationship between the actual position of the workpiece W at the capturing timing of the input image 33B and the omnidirectional camera 300. Subsequently, the inspector 154 compares the workpiece W shown at the identified position with the reference image associated with the direction of the workpiece W, and then inspects the workpiece W based on a result of the comparison. Identifying a workpiece portion shown in the input image and then comparing the workpiece portion with the reference image makes the processing time required for the inspection process shorter than scanning the reference image 135A in the input image 33B.

[D. Control Configuration of Controller 100]

Figure 11:
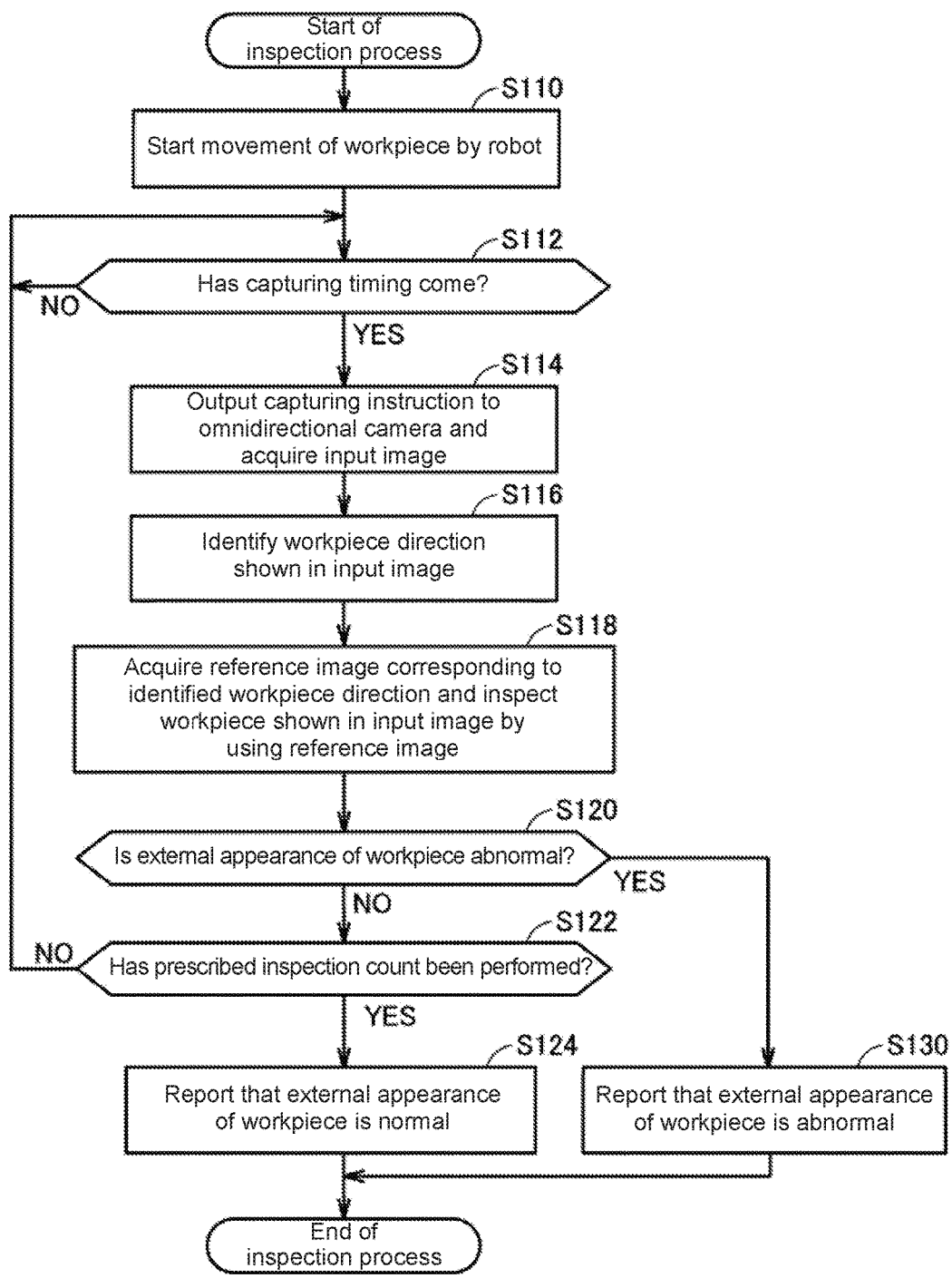
FIG. 11 is a flowchart illustrating an inspection process by a controller according to a first embodiment.

The inspection process by the controller 100 will be described with reference to FIG. 11. FIG. 11 is a flowchart illustrating the inspection process by the controller 100. The process illustrated in FIG. 11 is implemented by the processor 102 of the controller 100 (refer to FIG. 5) executing a program. In other aspects, part or all of the process may be executed by a circuit element or other hardware.

In step S110, the processor 102 starts movement of the workpiece W by the robot 200 based on receipt of an instruction to execute the inspection process. The workpiece W circles around the omnidirectional camera 300 in the movement process.

In step S112, the processor 102 determines whether the capturing timing has come. As one example, the capturing timing comes at constant time intervals after the workpiece W reaches the circling trajectory of the omnidirectional camera 300. When the processor 102 determines that the capturing timing has come (YES in step S112), the processor 102 switches control to step S114. Otherwise (NO in step S112), the processor 102 executes the process of step S112 again.

In step S114, as the acquisition unit 150 (refer to FIG. 5), the processor 102 outputs the capturing instruction to the omnidirectional camera 300. The processor 102 then acquires the input image indicating the workpiece W from the omnidirectional camera 300.

In step S116, as the identification unit 152 (refer to FIG. 5), the processor 102 identifies the direction of the workpiece W shown in the input image acquired in step S114. The method for identifying the direction of the workpiece W has been described in FIG. 6 to FIG. 9, and thus descriptions thereof will not be repeated.

In step S118, as the inspector 154 (refer to FIG. 5), the processor 102 acquires the reference image associated with the direction of the workpiece W identified in step S116 with reference to the reference image information 135 (refer to FIG. 10). The processor 102 then compares the reference image with the input image. The comparison process between the reference image and the input image has been described in FIG. 10, and thus descriptions thereof will not be repeated.

In step S120, the processor 102 determines whether the external appearance of the workpiece W, which is an object to be inspected, is abnormal, based on a comparison result in step S118. As one example, the processor 102 determines that the external appearance of the workpiece W is abnormal when the similarity degree between the reference image and the input image is equal to or less than a value determined in advance. When the processor 102 determines that the external appearance of the workpiece W is abnormal (YES in step S120), the processor 102 switches control to step S130. Otherwise (NO in step S120), the processor 102 switches control to step S122.

In step S122, the processor 102 determines whether a prescribed inspection count has been performed on one workpiece W. The prescribed inspection count may be set in advance, and may be set arbitrarily. The prescribed inspection count corresponds to the capturing count on one workpiece W. When the processor 102 determines that the prescribed inspection count has been performed on one workpiece W (YES in step S122), the processor 102 switches control to step S124. Otherwise (NO in step S122), the processor 102 returns control to step S112.

In step S124, the processor 102 reports that the external appearance of the workpiece W is normal. Any method of the report may be used. As one example, the external appearance of the workpiece W being normal may be displayed as a message, and may be output as a sound.

In step S130, the processor 102 reports that the external appearance of the workpiece W is abnormal. Any method of the report may be used. As one example, the external appearance of the workpiece W being abnormal may be displayed as a message, and may be output as a sound.

[E. Hardware Configuration of Controller 100]

Figure 12:
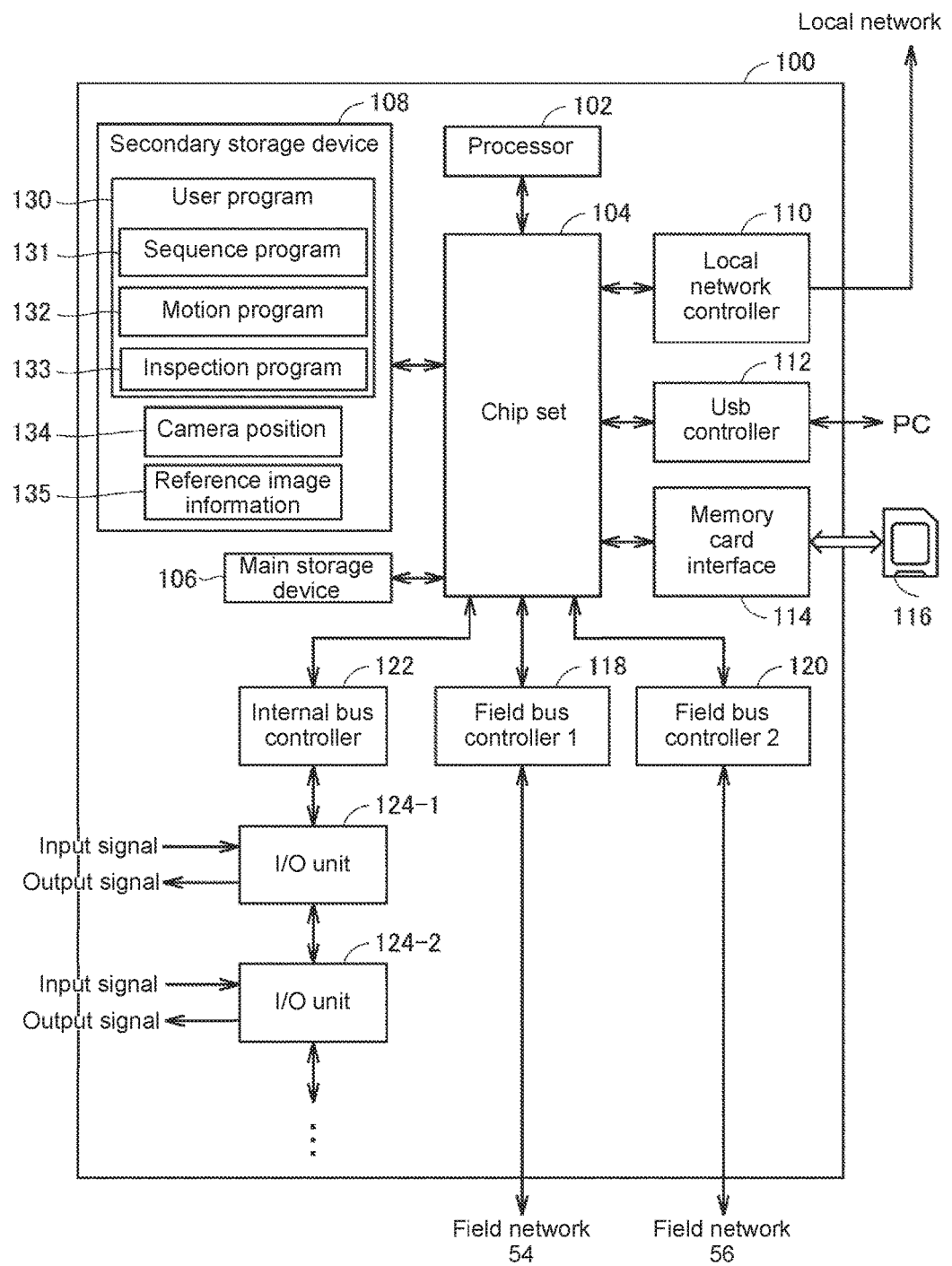
FIG. 12 is a block diagram illustrating a hardware configuration example of a controller according to a first embodiment.

With reference to FIG. 12, a hardware configuration of the controller 100 according to an embodiment will be described. FIG. 12 is a block diagram illustrating a hardware configuration example of the controller 100.

The controller 100 includes the processor 102 such as a central processing unit (CPU) or a micro-processing unit (MPU), a chip set 104, a main storage device 106, and a secondary storage device 108. The controller 100 also includes a local network controller 110, a universal serial bus (USB) controller 112, a memory card interface 114, an internal bus controller 122, field bus controllers 118 and 120, and I/O units 124-1 and 124-2.

The processor 102 reads various programs stored in the secondary storage device 108 and develops and executes the programs in the main storage device 106. Thus, the processor 102 implements control such as control according to an object to be controlled, and the inspection process. The chip set 104 controls the processor 102 and each component, thereby implementing process as the entire controller 100.

In addition to a system program for implementing a PLC engine, a user program 130 to be executed using the PLC engine is stored in the secondary storage device 108. Furthermore, the camera position 134 (refer to FIG. 5), the reference image information 135, and other information are stored in the secondary storage device 108. The user program 130 includes a sequence program 131 that mainly performs logical calculations, and a motion program 132 that mainly performs numerical calculations such as position control and speed control. In addition, the user program 130 includes an inspection program 133 that mainly performs calculations for implementing the inspection process of the workpiece, and other programs.

The local network controller 110 controls data exchange with other devices (for example, server) via a local network. The USB controller 112 controls data exchange with other devices (for example, personal computer (PC)) via USB connection.

The memory card interface 114 is configured such that a memory card 116 is detachable. The memory card interface 114 can write data into the memory card 116 and read various types of data (such as user program and trace data) from the memory card 116.

The internal bus controller 122 is an interface that exchanges data with the I/O units 124-1,124-2, and other I/O units mounted on the controller 100.

The field bus controller 118 controls data exchange with other devices (for example, image sensor 51, counter 52) via the field network 54. Similarly, the field bus controller 120 controls data exchange with other devices (for example, robot 200) via the field network 56.

FIG. 12 illustrates the configuration example in which necessary functions are provided by the processor 102 executing the programs. However, part or all of these provided functions may be mounted using dedicated hardware circuitry (for example, application specific integrated circuit (ASIC) or a field-programmable gate array (FPGA)). Alternatively, main parts of the controller 100 may be implemented using hardware according to general-purpose architecture (for example, industrial personal computer based on a general-purpose personal computer). In this case, a plurality of operating systems (OSs) for different applications may be executed in parallel using virtual technique, and necessary applications may be executed on each OS.

[F. Summary of First Embodiment]

As described above, the controller 100 according to an embodiment instructs the robot 200 to cause the workpiece W to circle around the omnidirectional camera 300 in the state where the posture of the object to be inspected is maintained. The controller 100 outputs the capturing instruction to the omnidirectional camera 300 at a plurality of timings while the robot 200 is causing the workpiece W to circle around the omnidirectional camera 300. At this time, since the posture of the workpiece W is maintained, the external appearance of the workpiece W when viewed from the omnidirectional camera 300 changes at each position of the workpiece W. Therefore, the plurality of input images indicating the workpiece W from different directions is obtained. The controller 100 inspects the workpiece W by using the plurality of input images.

Thus, by outputting the capturing instruction to the omnidirectional camera 300 at different timings while the workpiece W is circling around, the controller 100 can acquire, from one omnidirectional camera 300, the input images 30A to 30D indicating the workpiece W from different directions.

<Second Embodiment>

[A. Outline]

In a first embodiment, the robot 200 has caused the workpiece W to circle around the omnidirectional camera 300. In contrast, in a second embodiment, a conveyor 200A causes a workpiece W to circle around an omnidirectional camera 300. This allows the omnidirectional camera 300 to capture a plurality of workpieces W simultaneously.

Other points have been described in "first embodiment", and thus descriptions thereof will not be repeated below.

[B. Capturing Process of Workpiece W]

Figure 13:
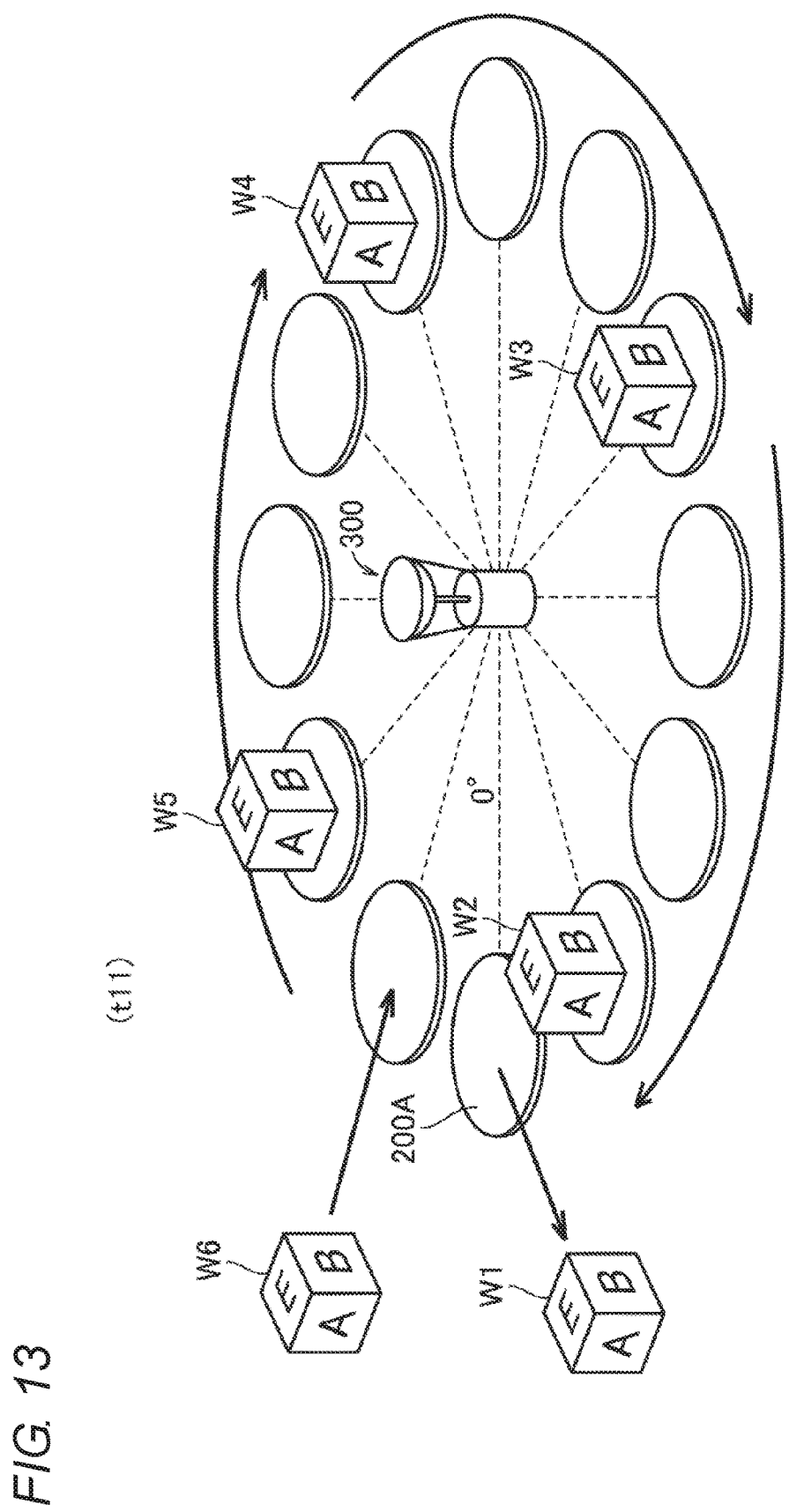
FIG. 13 is a view illustrating how a conveyor that serves as a movement device conveys workpieces W.
Figure 14:
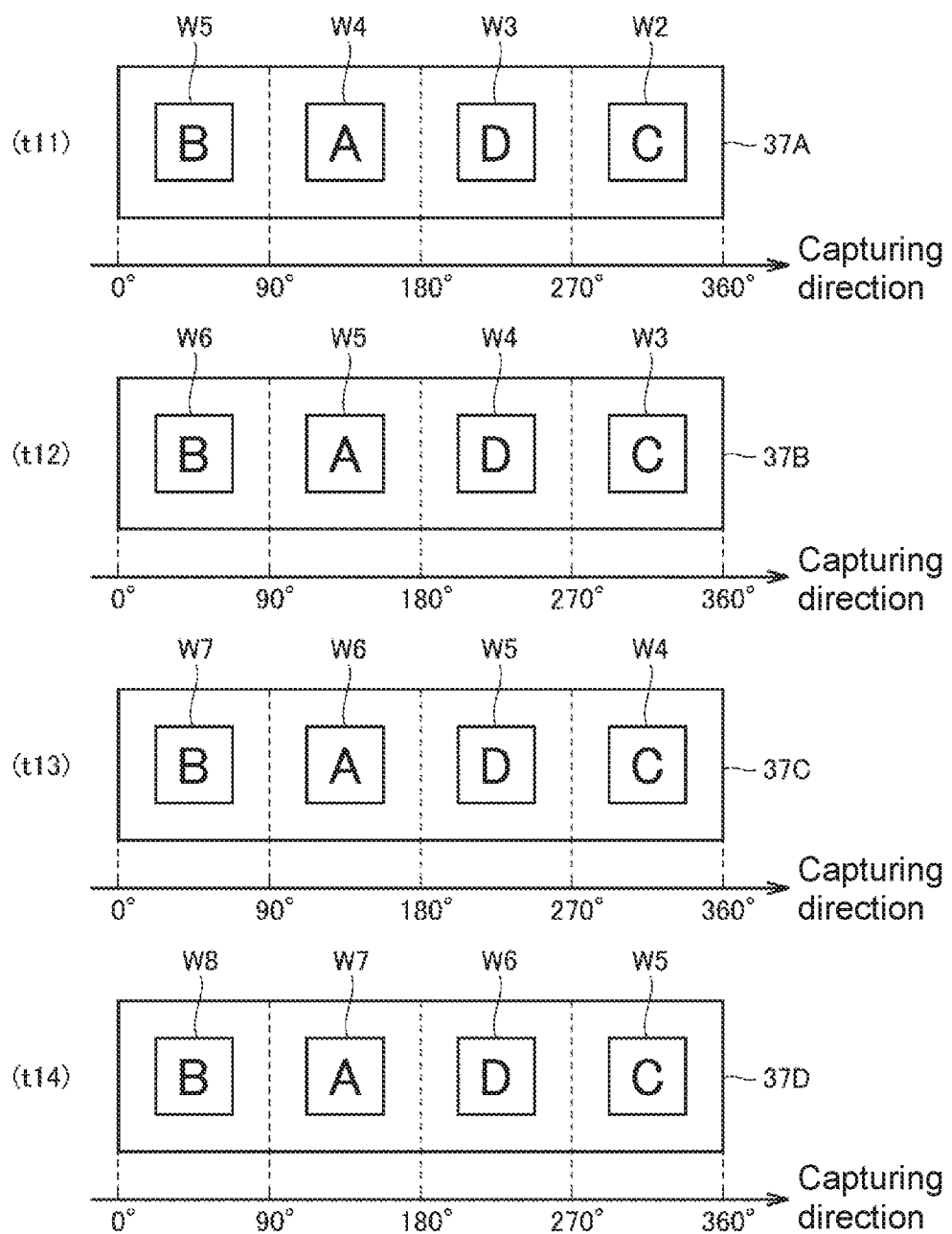
FIG. 14 is a diagram illustrating one example of input images obtained from an omnidirectional camera according to a second embodiment.

With reference to FIGS. 13 and 14, a capturing process of workpieces W in a second embodiment will be described.

FIG. 13 is a view illustrating how a conveyor 200A that serves as a movement device conveys workpieces W. FIG. 13 illustrates workpieces W1 to W6 as one example of objects to be inspected. In an embodiment, the conveyor 200A causes the plurality of workpieces W1 to W6 to be simultaneously conveyed around the omnidirectional camera 300. At this time, the conveyor 200A causes the workpieces W1 to W6 to circle around the omnidirectional camera 300 in a state where postures of the workpieces W1 to W6 are maintained. Since the postures of the workpieces W1 to W6 are maintained, the external appearance of each workpiece when viewed from the omnidirectional camera 300 changes at each workpiece position.

The controller 100 outputs a capturing instruction to the omnidirectional camera 300 at a plurality of timings while the workpieces W1 to W6 are circling around. This allows the omnidirectional camera 300 to capture the workpieces from various directions. As a result, the controller 100 can acquire a plurality of input images indicating the workpieces from different directions.

FIG. 14 is a diagram illustrating one example of input images obtained from the omnidirectional camera 300 according to a second embodiment. As one example, it is assumed that the controller 100 outputs the capturing instruction to the omnidirectional camera 300 at timing t11. As a result, an input image 37A is obtained indicating "a C surface" of the workpiece W2, "a D surface" of the workpiece W3, "an A surface" of the workpiece W4, and "a B surface" of the workpiece W5. It is assumed that the controller 100 outputs the capturing instruction to the omnidirectional camera 300 at timing t12. As a result, an input image 37B is obtained indicating "the C surface" of the workpiece W3, "the D surface" of the workpiece W4, "the A surface" of the workpiece W5, and "the B surface" of the workpiece W6. It is assumed that the controller 100 outputs the capturing instruction to the omnidirectional camera 300 at timing t13. As a result, an input image 37C is obtained indicating "the C surface" of the workpiece W4, "the D surface" of the workpiece W5, "the A surface" of the workpiece W6, and "the B surface" of the workpiece W7. It is assumed that the controller 100 outputs the capturing instruction to the omnidirectional camera 300 at timing t14. As a result, an input image 37D is obtained indicating "the C surface" of the workpiece W5, "the D surface" of the workpiece W6, "the A surface" of the workpiece W7, and "the B surface" of the workpiece W8.

Intervals at which the capturing instruction is output are calculated, for example, by dividing, by a capturing count, a circling time needed for the conveyor 200A to cause each workpiece to circle around (in a full circle). For example, when the circling time is one second and the capturing count is four times, the capturing interval will be 0.25 seconds (=¼). The circling time and the capturing count may be set in advance, and may be set arbitrarily.

Thus, by outputting the capturing instruction to the omnidirectional camera 300 at different timings while the workpieces W1 to W6 are circling around, the controller 100 can acquire, from one omnidirectional camera 300, the plurality of input images indicating each workpiece from different directions.

Typically, the conveyor 200A conveys the workpieces such that each workpiece direction when the workpiece reaches the circling trajectory is always identical. As a result, as illustrated in FIG. 14, the same surface of each workpiece is shown at the same position in the input images 37A to 37D.

Note that although FIG. 13 illustrates the example in which the workpieces W1 to W6 circle around the omnidirectional camera 300 in a full circle, the workpieces W1 to W6 do not necessarily have to circle around the omnidirectional camera 300 in a full circle. That is, the workpieces W1 to W6 are at least required to circle around the omnidirectional camera 300 in part of a circle in the state where the postures are maintained.

[C. Inspection Process of Workpiece W]

Figure 15:
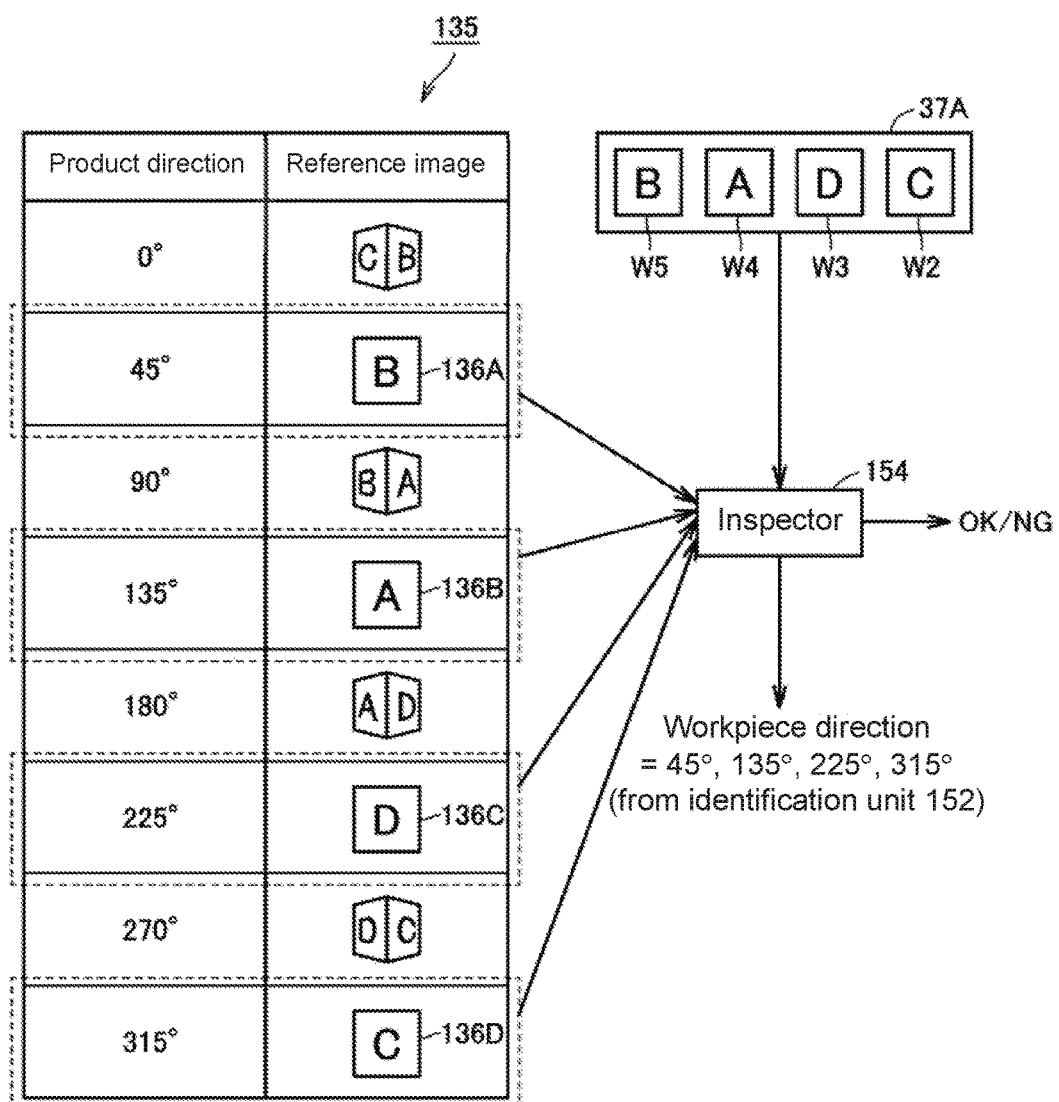
FIG. 15 is a conceptual diagram schematically illustrating an inspection process of a workpiece according to a second embodiment.

With reference to FIG. 15, the inspection process of the workpiece by the inspector 154 (refer to FIG. 5) according to a second embodiment will be described. FIG. 15 is a conceptual diagram schematically illustrating the inspection process of the workpiece according to a second embodiment.

FIG. 15 illustrates, as one example of the input images, the input image 37A obtained by simultaneously capturing "the C surface" of the workpiece W2, "the D surface" of the workpiece W3, "the A surface" of the workpiece W4, and "the B surface" of the workpiece W5. The inspection process by the inspector 154 will be described below by citing, as an example, the input image 37A, which is one of the obtained input images.

The identification unit 152 (refer to FIG. 5) identifies directions of the workpieces W2 to W5 shown in the input image 37A. As a method for identifying each workpiece direction, "the first to third identification methods" described in "first embodiment" are employed. Each workpiece direction identified by the identification unit 152 is output to the inspector 154. In the example of FIG. 15, "45°", "135°", "225°", and "315°" are output to the inspector 154 as each workpiece direction.

The inspector 154 inspects the workpieces W2 to W5 shown in the input image 37A with reference to the reference image information 135. The reference image information 135 includes a plurality of reference images obtained by capturing in advance an object of a type identical to an object to be inspected. Each reference image is associated with an object direction shown in the reference image. The reference image information 135 is prepared in advance before the inspection process is executed. For example, the reference image information 135 is stored in advance in a device such as the secondary storage device 108 of the controller 100 (refer to FIG. 12).

The inspector 154 identifies the reference images corresponding to the directions of the workpieces W shown in the input image 37A with reference to the reference image information 135. In the example of FIG. 15, a reference image 136A corresponding to a workpiece direction "45°" and a reference image 136B corresponding to a workpiece direction "135°" are identified. Also, a reference image 136C corresponding to a workpiece direction "225°" and a reference image 136D corresponding to a workpiece direction "315°" are identified. The inspector 154 compares each of the identified reference images 136A to 136D with the input image 37A, and then inspects the workpieces W2 to W5 shown in the input image 37A based on a result of the comparison. The comparison process between the reference image and the input image has been described in FIG. 10, and thus descriptions thereof will not be repeated.

The inspector 154 executes the comparison process between the reference images and all of the plurality of input images acquired by the acquisition unit 150. Typically, the inspector 154 extracts the same workpiece from each input image, and then calculates a similarity degree between each extracted workpiece portion and the corresponding reference image. For example, when performing inspection on the workpiece W5, the inspector 154 performs the following calculations. The inspector 154 calculates the similarity degree between the workpiece W5 in the input image 37A and the reference image 136A. Also, the inspector 154 calculates the similarity degree between the workpiece W5 in the input image 37B (refer to FIG. 14) and the reference image 136B. Also, the inspector 154 calculates the similarity degree between the workpiece W5 in the input image 37C (refer to FIG. 14) and the reference image 136C. Also, the inspector 154 calculates the similarity degree between the workpiece W5 in the input image 37D (refer to FIG. 14) and the reference image 136D. Then, when all the similarity degrees calculated about the workpiece W5 exceed a value determined in advance, the inspector 154 determines that the external appearance of the workpiece W5 is normal. On the other hand, when at least one of the similarity degrees calculated about the workpiece W5 is equal to or less than the value determined in advance, the inspector 154 determines that the external appearance of the workpiece W5 is abnormal.

[D. Control Configuration of Controller 100]

Figure 16:
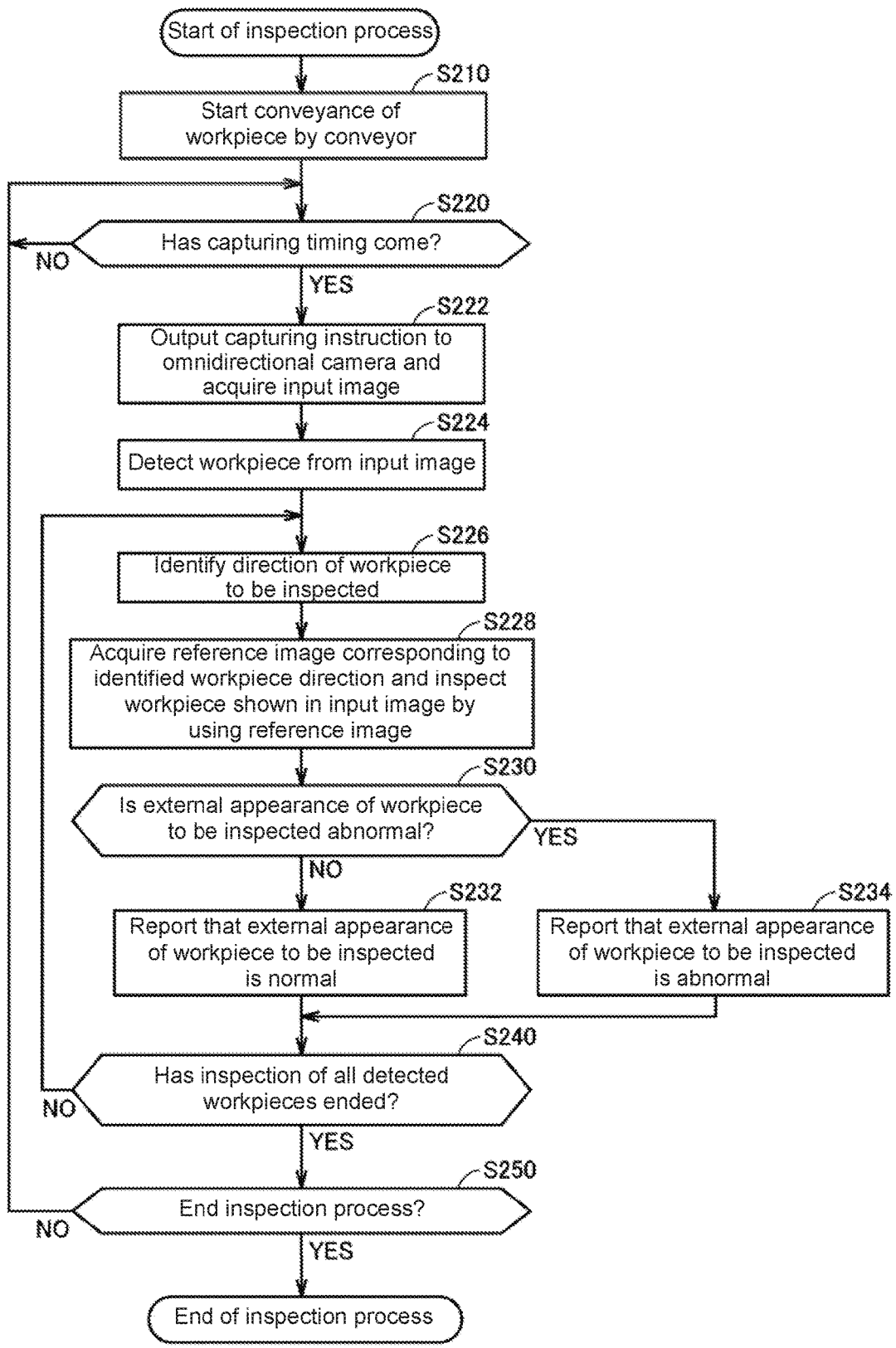
FIG. 16 is a flowchart illustrating an inspection process by a controller according to a second embodiment.

With reference to FIG. 16, the inspection process by the controller 100 according to a second embodiment will be described. FIG. 16 is a flowchart illustrating the inspection process by the controller 100 according to a second embodiment. The process illustrated in FIG. 16 is implemented by the processor 102 of the controller 100 (refer to FIG. 5) executing a program. In other aspects, part or all of the process may be executed by a circuit element or other hardware.

In step S210, the processor 102 starts conveyance of the workpiece by the conveyor 200A based on receipt of an instruction to execute the inspection process. The workpiece circles around the omnidirectional camera 300 in the conveyance process.

In step S220, the processor 102 determines whether the capturing timing has come. The capturing timing comes, for example, at constant time intervals. When the processor 102 determines that the capturing timing has come (YES in step S220), the processor 102 switches control to step S222. Otherwise (NO in step S220), the processor 102 executes the process of step S220 again.

In step S222, as the acquisition unit 150 (refer to FIG. 5), the processor 102 outputs the capturing instruction to the omnidirectional camera 300. The processor 102 then acquires the input image indicating the workpiece from the omnidirectional camera 300.

In step S224, the processor 102 detects the workpiece from the input image acquired in step S222. As illustrated in FIG. 1, the processor 102 grasps each workpiece position on the conveyor 200A by a tracking process. The position of each workpiece on the conveyor 200A corresponds to the position of each workpiece in the input image. Therefore, the processor 102 can identify the position of each workpiece in the input image from the position of each workpiece on the conveyor 200A identified by the tracking process. Note that the processor 102 may identify the workpiece position in the input image by using an image processing technology such as template matching.

In step S226, as the identification unit 152 (refer to FIG. 5), the processor 102 determines any one uninspected workpiece from the workpiece detected in step S224 as the workpiece to be inspected. The processor 102 then identifies the direction of the workpiece to be inspected. As a method for identifying the workpiece direction, "the first to third identification methods" described in "first embodiment" are employed.

In step S228, as the inspector 154 (refer to FIG. 5), the processor 102 acquires a reference image corresponding to the workpiece direction identified in step S226 with reference to the reference image information 135 (refer to FIG. 15). The processor 102 then compares the reference image with the input image. The comparison process between the reference image and the input image has been described in FIG. 15, and thus descriptions thereof will not be repeated.

In step S230, the processor 102 determines whether the external appearance of the workpiece, which is an object to be inspected, is abnormal, based on a result of the comparison in step S228. As one example, the processor 102 determines that the external appearance of the workpiece to be inspected is abnormal when the similarity degree between the reference image and the input image is equal to or less than a value determined in advance. When the processor 102 determines that the external appearance of the workpiece to be inspected is abnormal (YES in step S230), the processor 102 switches control to step S234. Otherwise (NO in step S230), the processor 102 switches control to step S232.

In step S232, the processor 102 reports that the external appearance of the workpiece to be inspected is normal. Any method of the report may be used. As one example, the external appearance of the workpiece being normal may be displayed as a message, and may be output as a sound.

In step S234, the processor 102 reports that the external appearance of the workpiece to be inspected is abnormal. Any method of the report may be used. As one example, the external appearance of the workpiece being abnormal may be displayed as a message, and may be output as a sound.

In step S240, the processor 102 determines whether inspection of all the workpieces detected in step S224 has ended. When the processor 102 determines that inspection of all the workpieces detected in step S224 has ended (YES in step S240), the processor 102 switches control to step S250. Otherwise (NO in step S240), the processor 102 returns control to step S226.

In step S250, the processor 102 determines whether to end the inspection process. As one example, when the processor 102 receives an operation to end the inspection process, the processor 102 determines to end the inspection process. When the processor 102 determines to end the inspection process (YES in step S250), the processor 102 ends the inspection process illustrated in FIG. 16. Otherwise (NO in step S250), the processor 102 returns control to step S220.

[E. Summary of Second Embodiment]

As described above, in a second embodiment, the conveyor 200A causes the workpieces, which are objects to be inspected, to circle around the omnidirectional camera 300. This allows the omnidirectional camera 300 to capture the plurality of workpieces simultaneously, and to inspect the plurality of workpieces simultaneously.

Also, the conveyor 200A causes each workpiece to circle around the omnidirectional camera 300 in a state where the posture of the workpiece is maintained. The controller 100 outputs the capturing instruction to the omnidirectional camera 300 at a plurality of timings while the workpiece is circling around. This allows the omnidirectional camera 300 to capture each workpiece from various directions. As a result, for each workpiece, the controller 100 can acquire the plurality of input images indicating the workpiece from different directions.

<Third Embodiment>

[Outline]

In a first embodiment, a shape of a workpiece W, which is an object to be inspected, has been a cube. In contrast, in a third embodiment, a shape of a workpiece W, which is an object to be inspected, is cylindrical. When the workpiece is cylindrical, even if a side surface of the workpiece is captured from different directions, the shape of the workpiece shown in an image does not change. Therefore, the controller 100 according to a third embodiment does not identify a workpiece direction when the shape of the object to be inspected is cylindrical. This shortens processing time.

Other points have been described in "first embodiment", and thus descriptions thereof will not be repeated below.

[B. Capturing Process of Workpiece W]

Figure 17:
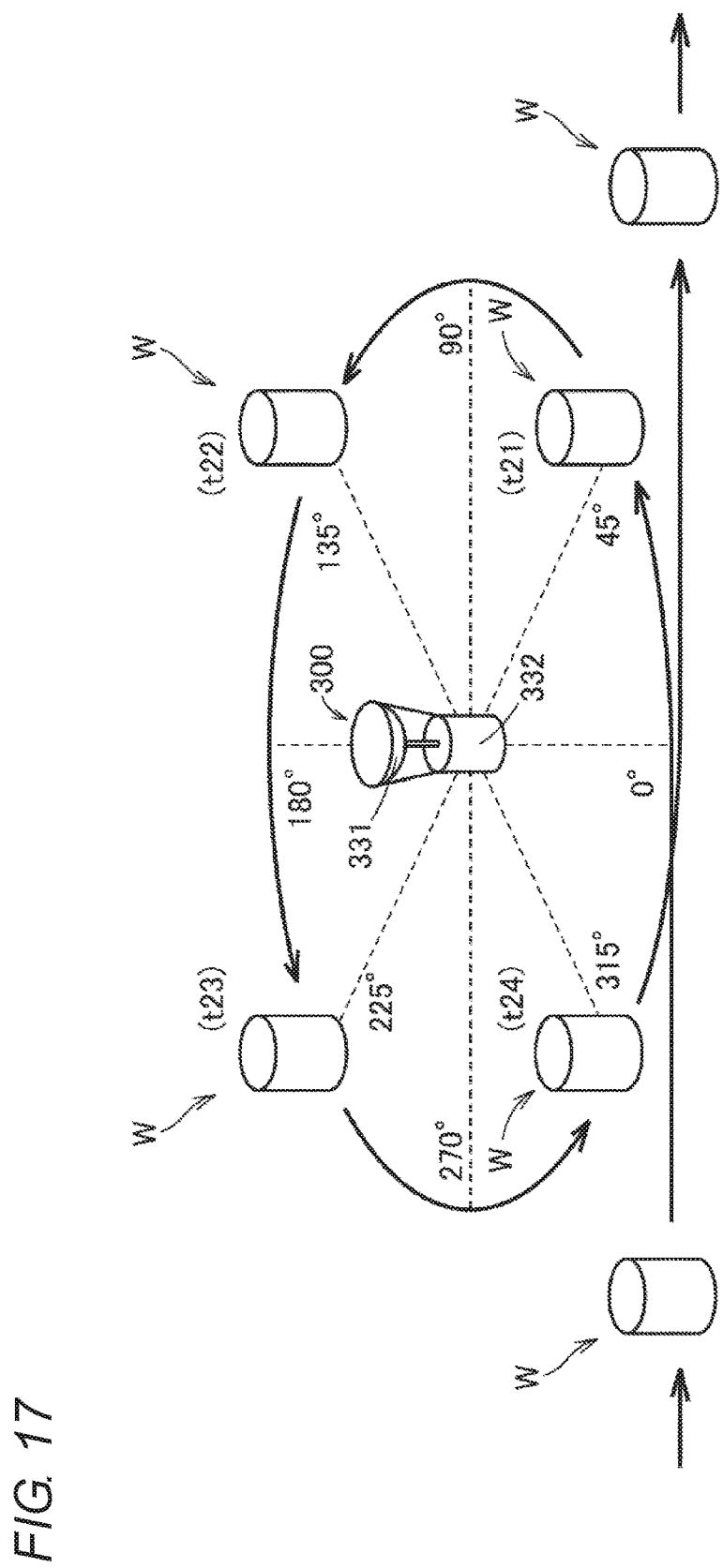
FIG. 17 is a view illustrating a process in which a robot according to a third embodiment causes a workpiece to circle around an omnidirectional camera.
Figure 18:
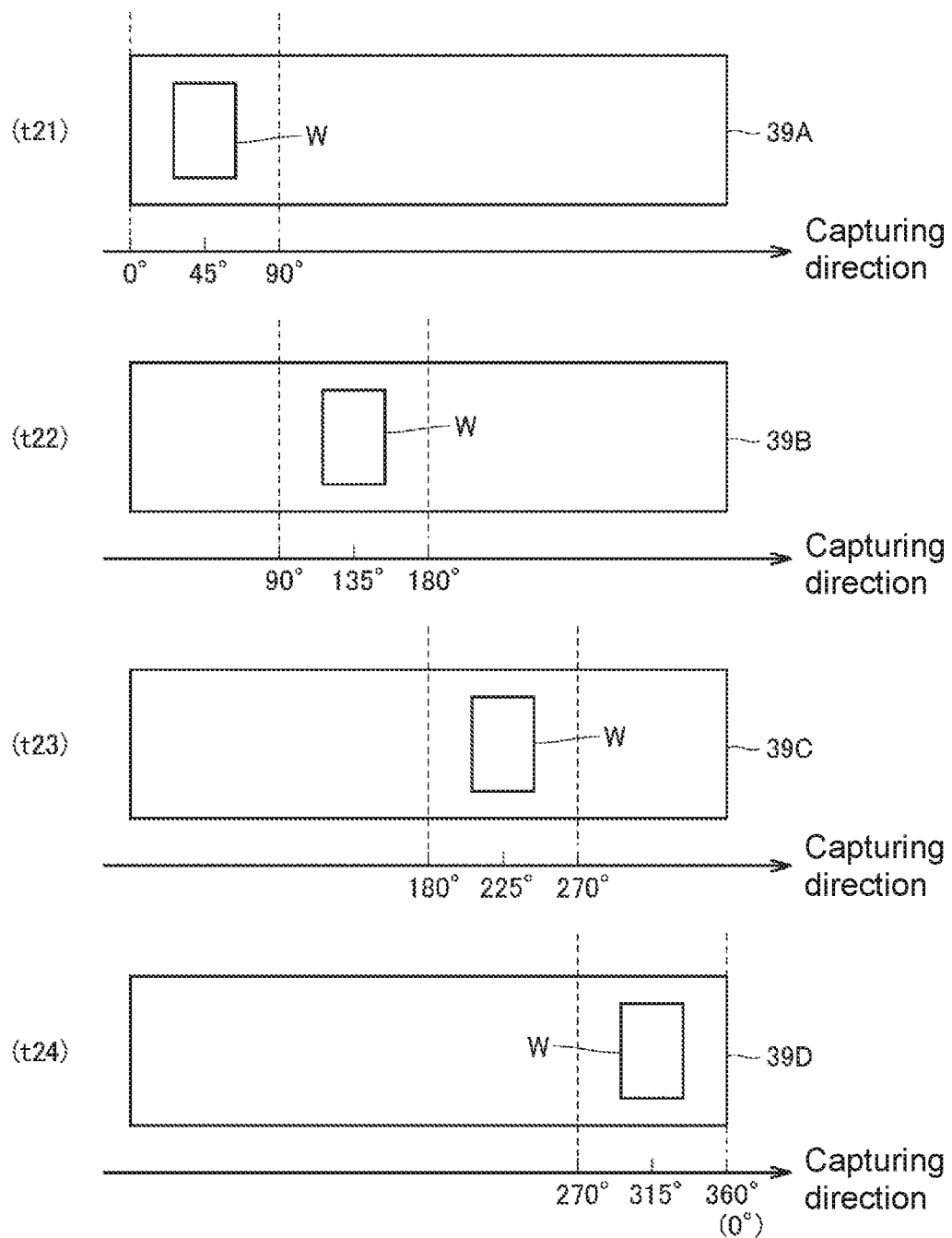
FIG. 18 is a diagram illustrating one example of input images obtained from an omnidirectional camera according to a third embodiment.

With reference to FIGS. 17 and 18, a capturing process of the workpiece W in a third embodiment will be described.

FIG. 17 is a view illustrating a process in which a robot 200 according to a third embodiment causes the workpiece W to circle around an omnidirectional camera 300. As illustrated in FIG. 17, in an embodiment, the shape of the workpiece W is cylindrical. The controller 100 outputs a capturing instruction to the omnidirectional camera 300 at a plurality of timings while the workpiece W is circling around the omnidirectional camera 300. This allows the omnidirectional camera 300 to capture the workpiece W from various directions. As a result, the controller 100 can acquire, from the omnidirectional camera 300, a plurality of input images indicating the workpiece W from different directions.

FIG. 18 is a diagram illustrating one example of input images obtained from the omnidirectional camera 300 according to a third embodiment. As one example, it is assumed that the controller 100 outputs the capturing instruction to the omnidirectional camera 300 at timing t21. As a result, an input image 39A is obtained. Similarly, it is assumed that the controller 100 outputs the capturing instruction to the omnidirectional camera 300 at timing t22. As a result, an input image 39B is obtained. Similarly, it is assumed that the controller 100 outputs the capturing instruction to the omnidirectional camera 300 at timing t23. As a result, an input image 39C is obtained. Similarly, it is assumed that the controller 100 outputs the capturing instruction to the omnidirectional camera 300 at timing t24. As a result, an input image 39D is obtained.

As illustrated in the input images 39A to 39D, when the workpiece W is cylindrical, even if a side surface of the workpiece W is captured from different directions, the shape of the workpiece W shown in the input images does not change. Therefore, the controller 100 according to an embodiment does not need to identify the workpiece direction shown in the input images. Also, in an embodiment, it is not necessary to prepare the reference image for each direction of the workpiece W, and it is sufficient if at least one reference image is prepared.

The controller 100 compares each of the input images obtained by capturing the workpiece W from various directions with the reference image prepared in advance, and then inspects the workpiece W based on a result of the comparison. This allows the controller 100 to inspect the cylindrical workpiece W from every direction.

[Summary of Third Embodiment]

As described above, when the workpiece is cylindrical, even if the side surface of the workpiece is captured from different directions, the shape of the workpiece shown in the input images does not change. Therefore, the controller 100 according to an embodiment does not identify the workpiece direction, when the shape of the object to be inspected is cylindrical. This shortens processing time.

<Fourth Embodiment>

In a first embodiment, the robot 200 has caused the workpiece W to circle around the omnidirectional camera 300 in a circle. In contrast, in a fourth embodiment, a robot 200 causes a workpiece W to circle around an omnidirectional camera 300 in a square.

Figure 19:
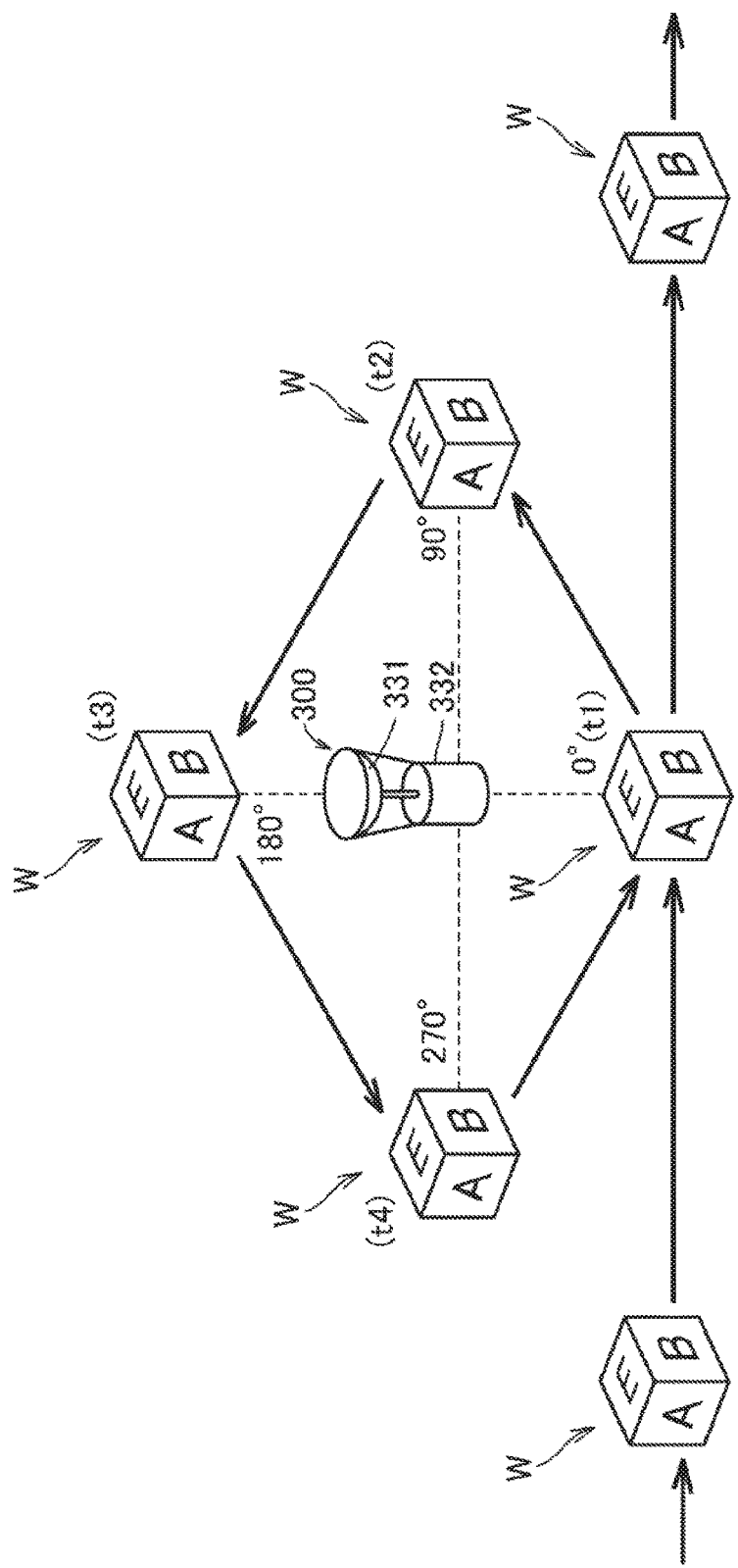
FIG. 19 is a view illustrating how a robot according to a fourth embodiment causes a workpiece to circle around an omnidirectional camera in a square.

FIG. 19 is a view illustrating how the robot 200 causes the workpiece W to circle around the omnidirectional camera 300 in a square. Thus, a circling trajectory of the workpiece W is not limited to circular. In a state where a posture of the workpiece W is maintained, the circling trajectory of the workpiece W is arbitrary. For example, the circling trajectory of the workpiece W may be elliptical, rectangular, or any other shapes.

The embodiments disclosed this time are to be considered in all respects as illustrative and not restrictive. The scope of the invention is indicated by the appended claims rather than by the foregoing description, and all changes which come within the meaning and range of equivalency of the claims are therefore intended to be embraced therein.

The invention claimed is:

1. An inspection system for inspecting an object to be inspected, the inspection system comprising:
    an omnidirectional camera;
    a movement device configured to cause the object to circle around the omnidirectional camera such that the object maintains a fixed direction so as not to rotate, while the object changes a direction relative to the omnidirectional camera as the object circles around the omnidirectional camera; and
    a processor configured with a program to perform operations comprising:
        operation as an acquisition unit configured to output a capturing instruction to the omnidirectional camera at a plurality of times while the movement device causes the object to circle around the omnidirectional camera, the acquisition unit being configured to acquire, from the omnidirectional camera, a plurality of input images comprising images of the object viewed from different directions; and
        operation as an inspector configured to inspect the object to be inspected by using the plurality of input images.

2. The inspection system according to claim 1, wherein the movement device causes the object to circle around the omnidirectional camera such that a constant distance is maintained from the omnidirectional camera to the object.

3. The inspection system according to claim 2, wherein the movement device does not stop the object while the object is circling around the omnidirectional camera.

4. The inspection system according to claim 3, wherein the processor is configured with the program to perform operations further comprising:
    operation as a storage configured to associate and store a plurality of reference images, captured in advance, of an object of a type identical to the object; and
    operation as an identification unit configured to identify a first direction of the object shown in a first input image of the plurality of input images and a second direction of the object shown in a second input image of the plurality of input images,
    wherein the processor is configured with the program such that operation as the inspector comprises operation as the inspector that:
    compares a reference image associated with the first direction from the plurality of reference images with the first input image;
    compares a reference image associated with the second direction from the plurality of reference images with the second input image; and
    inspects the object based on a result of the comparison.

5. The inspection system according to claim 2, wherein the processor is configured with the program to perform operations further comprising:
    operation as a storage configured to associate and store a plurality of reference images, captured in advance, of an object of a type identical to the object; and
    operation as an identification unit configured to identify a first direction of the object shown in a first input image of the plurality of input images and a second direction of the object shown in a second input image of the plurality of input images,
    wherein the processor is configured with the program such that operation as the inspector comprises operation as the inspector that:
    compares a reference image associated with the first direction from the plurality of reference images with the first input image;
    compares a reference image associated with the second direction from the plurality of reference images with the second input image; and
    inspects the object based on a result of the comparison.

6. The inspection system according to claim 1, wherein the movement device does not stop the object while the object is circling around the omnidirectional camera.

7. The inspection system according to claim 6, wherein the processor is configured with the program to perform operations further comprising:
    operation as a storage configured to associate and store a plurality of reference images, captured in advance, of an object of a type identical to the object; and
    operation as an identification unit configured to identify a first direction of the object shown in a first input image of the plurality of input images and a second direction of the object shown in a second input image of the plurality of input images,
    wherein the processor is configured with the program such that operation as the inspector comprises operation as the inspector that:
    compares a reference image associated with the first direction from the plurality of reference images with the first input image;
    compares a reference image associated with the second direction from the plurality of reference images with the second input image; and
    inspects the object based on a result of the comparison.

8. The inspection system according to claim 1, wherein the processor is configured with the program to perform operations further comprising:

operation as a storage configured to associate and store a plurality of reference images, captured in advance, of an object of a type identical to the object; and operation as an identification unit configured to identify a first direction of the object shown in a first input image of the plurality of input images and a second direction of the object shown in a second input image of the plurality of input images, wherein the processor is configured with the program such that operation as the inspector comprises operation as the inspector that:

compares a reference image associated with the first direction from the plurality of reference images with the first input image;

compares a reference image associated with the second direction from the plurality of reference images with the second input image; and inspects the object based on a result of the comparison.

9. The inspection system according to claim 8, wherein the processor is configured with the program such that operation as the identification unit comprises operation as the identification unit that:

identifies the first direction based on a position of the object at a capturing time of the first input image, and a position of the omnidirectional camera; and identifies the second direction based on a position of the object at a capturing time of the second input image, and the position of the omnidirectional camera.

10. The inspection system according to claim 8, wherein the movement device, comprises a plurality of marks located at different positions on a surface of the movement device, the plurality of marks are associated in advance with directions of the object, and the processor is configured with the program such that operation as the identification unit comprises operation as the identification unit that:

identifies each of the directions associated with each of the marks shown in the first input image as the first direction; and identifies each of the directions associated with each of the marks shown in the second input image as the second direction.

11. The inspection system according claim 8, wherein the processor is configured with the program such that operation as the inspector comprises operation as the inspector that:

identifies a position of the object shown in the first input image based on a positional relationship between the position of the object at a capturing time of the first input image and the omnidirectional camera, the inspector comparing the object shown at the position with the reference image associated with the first direction;

identifies the position of the object shown in the second input image based on a positional relationship between the position of the object at a capturing time of the second input image and the omnidirectional camera, the inspector comparing the object shown at the position with the reference image associated with the second direction; and inspects the object based on a result of the comparison.

12. A controller for controlling a movement device for moving an object to be inspected and an omnidirectional camera for capturing the object, the controller configured with a program to perform operations comprising:

operation as an acquisition unit configured to output, to the movement device, an instruction for causing the object to circle around the omnidirectional camera such that the object maintains a fixed direction so as not to rotate, while the object changes a direction relative to the omnidirectional camera as the object circles around the omnidirectional camera, to output a capturing instruction to the omnidirectional camera at a plurality of times while the movement device causes the object to circle around the omnidirectional camera, and to acquire, from the omnidirectional camera, a plurality of input images comprising images of the object viewed from different directions; and operation as an inspector configured to inspect the object by using the plurality of input images.

13. An inspection method for inspecting an object to be inspected, the inspection method comprising:

causing the object to circle around an omnidirectional camera such that the object maintains a fixed direction so as not to rotate, while the object changes a direction relative to the omnidirectional camera as the object circles around the omnidirectional camera;

outputting a capturing instruction to the omnidirectional camera at a plurality of times while the object is circling around the omnidirectional camera, and acquiring, from the omnidirectional camera, a plurality of input images comprising images of the object viewed from different directions; and inspecting the object by using the plurality of input images.

14. The inspection method according to claim 13, wherein causing the object to circle around the omnidirectional camera comprises causing the object to circle around the omnidirectional camera such that the object maintains a fixed direction so as not to rotate, while the object changes a direction relative to the omnidirectional camera as the object circles around the omnidirectional camera such that a constant distance is maintained from the omnidirectional camera to the object.

15. The inspection method according to claim 13, wherein causing the object to circle around the omnidirectional camera comprises causing the object to circle around the omnidirectional camera such that the object maintains a fixed direction so as not to rotate, while the object changes a direction relative to the omnidirectional camera as the object circles around the omnidirectional camera such that the object does not stop while the object is circling around the omnidirectional camera.

16. The inspection method according to claim 13, further comprising:

capturing, in advance, a plurality of reference images of an object of a type identical to the object;

identifying a first direction of the object shown in a first input image of the plurality of input images and a second direction of the object shown in a second input image of the plurality of input images;

comparing a reference image associated with the first direction from the plurality of reference images with the first input image;

comparing a reference image associated with the second direction from the plurality of reference images with the second input image; and inspecting the object based on a result of the comparison.

17. The inspection method according to claim 16, further comprising:

identifying the first direction based on a position of the object at a capturing time of the first input image, and a position of the omnidirectional camera; and identifying the second direction based on a position of the object at a capturing time of the second input image, and the position of the omnidirectional camera.

18. A non-transitory computer-readable storage medium storing an inspection program for inspecting an object to be inspected, the inspection program causing a computer to perform operations comprising:
  causing the object to circle around an omnidirectional camera such that the object maintains a fixed direction so as not to rotate, while the object changes a direction relative to the omnidirectional camera as the object circles around the omnidirectional camera;
  outputting a capturing instruction to the omnidirectional camera at a plurality of times while the object is circling around the omnidirectional camera, and acquiring, from the omnidirectional camera, a plurality of input images comprising images of the object viewed from different directions; and
  inspecting the object by using the plurality of input images.

* * * * *